(12) United States Patent
Kowalczyk et al.

(10) Patent No.: US 12,336,914 B2
(45) Date of Patent: Jun. 24, 2025

(54) BONE FIXATION DEVICE

(71) Applicant: Paragon Advanced Technologies, Inc., Englewood, CO (US)

(72) Inventors: Gregory J. Kowalczyk, Little Silver, NJ (US); Brian R. McLaughlin, Yarmouth, ME (US); Selene G. Parekh, Durham, NC (US); Luciano Bernardino Bertolotti, Denver, CO (US)

(73) Assignee: Paragon Advanced Technologies, Inc., Englewood, CO (US)

( * ) Notice: Subject to any disclaimer, the term of this patent is extended or adjusted under 35 U.S.C. 154(b) by 0 days.

(21) Appl. No.: 18/474,343

(22) Filed: Sep. 26, 2023

(65) Prior Publication Data
US 2024/0091020 A1 Mar. 21, 2024

Related U.S. Application Data

(63) Continuation of application No. 17/313,206, filed on May 6, 2021, now Pat. No. 11,766,337, which is a
(Continued)

(51) Int. Cl.
*A61F 2/42* (2006.01)
*A61B 17/17* (2006.01)
(Continued)

(52) U.S. Cl.
CPC ........ *A61F 2/4202* (2013.01); *A61B 17/1775* (2016.11); *A61F 2/2846* (2013.01);
(Continued)

(58) Field of Classification Search
CPC .................. A61F 2/4202; A61F 2/4606; A61F 2002/30578; A61F 2002/368; A61B 17/1775
See application file for complete search history.

(56) References Cited

U.S. PATENT DOCUMENTS 4,715,860 A * 12/1987 Amstutz ............ A61B 17/1746
623/22.33
5,549,704 A * 8/1996 Sutter ................. A61F 2/30771
623/23.13
(Continued)

OTHER PUBLICATIONS

DukeHealth, 3D Printed Bone Implant Saves Woman's Leg (Year: 2015).*

*Primary Examiner* — Bruce E Snow
(74) *Attorney, Agent, or Firm* — Heslin Rothenberg Farley & Mesiti P.C.

(57) ABSTRACT

There is disclosed a bone fixation device that can include a cage having an optional mesh portion. The bone fixation device can be configured to couple a leg portion to a foot portion of a user's body. In at least one embodiment, the device includes at least one cage having a plurality of struts forming cells. There can be an optional mesh portion having a pre-set porosity that can be either constant or variable in density. In at least one embodiment there can be a cage portion which is substantially spherical shaped. Alternatively, the device can be substantially egg shaped. In at least one embodiment there can be a central post hole for receiving a post. In another embodiment at least one plate or shaft can connect to the cage.

21 Claims, 36 Drawing Sheets

Related U.S. Application Data continuation of application No. 16/268,074, filed on Feb. 5, 2019, now Pat. No. 11,147,679.

(60) Provisional application No. 62/626,525, filed on Feb. 5, 2018.

(51) Int. Cl.
*A61F 2/28* (2006.01)
*A61F 2/30* (2006.01)
*A61F 2/46* (2006.01)

(52) U.S. Cl.
CPC ...... *A61F 2/4606* (2013.01); *A61F 2002/285* (2013.01); *A61F 2002/30143* (2013.01); *A61F 2002/30242* (2013.01); *A61F 2002/30243* (2013.01); *A61F 2002/30286* (2013.01); *A61F 2002/30299* (2013.01); *A61F 2002/30322* (2013.01); *A61F 2002/30578* (2013.01); *A61F 2002/30593* (2013.01); *A61F 2002/30909* (2013.01); *A61F 2002/30919* (2013.01); *A61F 2002/3092* (2013.01); *A61F 2002/4205* (2013.01); *A61F 2002/421* (2013.01); *A61F 2/4607* (2013.01)

(56) References Cited

U.S. PATENT DOCUMENTS

| | | | |
|---|---|---|---|
| 9,636,226 B2* | 5/2017 | Hunt | A61F 2/4611 |
| 2009/0248084 A1* | 10/2009 | Hintermann | A61B 17/8004 |
| | | | 606/280 |
| 2014/0107785 A1* | 4/2014 | Geisler | A61F 2/442 |
| | | | 623/17.16 |

* cited by examiner

BONE FIXATION DEVICE

CROSS REFERENCE TO RELATED APPLICATIONS

This application is a continuation of U.S. patent application Ser. No. 17/313,206 filed on May 6, 2021, which is a continuation of U.S. patent application Ser. No. 16/268,074 filed on Feb. 5, 2019, which claims priority from U.S. Provisional Application No. 62/626,525 filed on Feb. 5, 2018, the entire disclosures of which are hereby expressly incorporated herein by reference.

BACKGROUND OF THE INVENTION

At least one embodiment relates to a bone fixation device which can in at least one embodiment be used to fix an ankle. In at least one embodiment, the bone fixation device is configured to be placed between a tibia portion of a person's leg and their foot portion. The bone fixation device can be used to fix or secure the leg portion of the person's body to a foot portion of the person's body using a structure which is configured to promote bone growth and healing in the joint region. Thus, there is a need for a bone fixation device which is used to fix a lower portion of a person's leg to a foot portion of the person's leg to heal a person's body in an ankle region.

SUMMARY OF THE INVENTION

There is disclosed a bone fixation device that can include a cage having an optional mesh portion. The bone fixation device can be configured to couple a leg portion to a foot portion of a user's body. In at least one embodiment, the device includes at least one cage having a plurality of struts forming cells. There can be an optional mesh portion having a pre-set porosity that can be either constant or variable in density. In at least one embodiment there can be a cage portion which is substantially spherical shaped. Alternatively, the device can be substantially egg shaped. In at least one embodiment there can be a central post hole for receiving a post. In another embodiment at least one plate or shaft can connect to the cage.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figure 1:
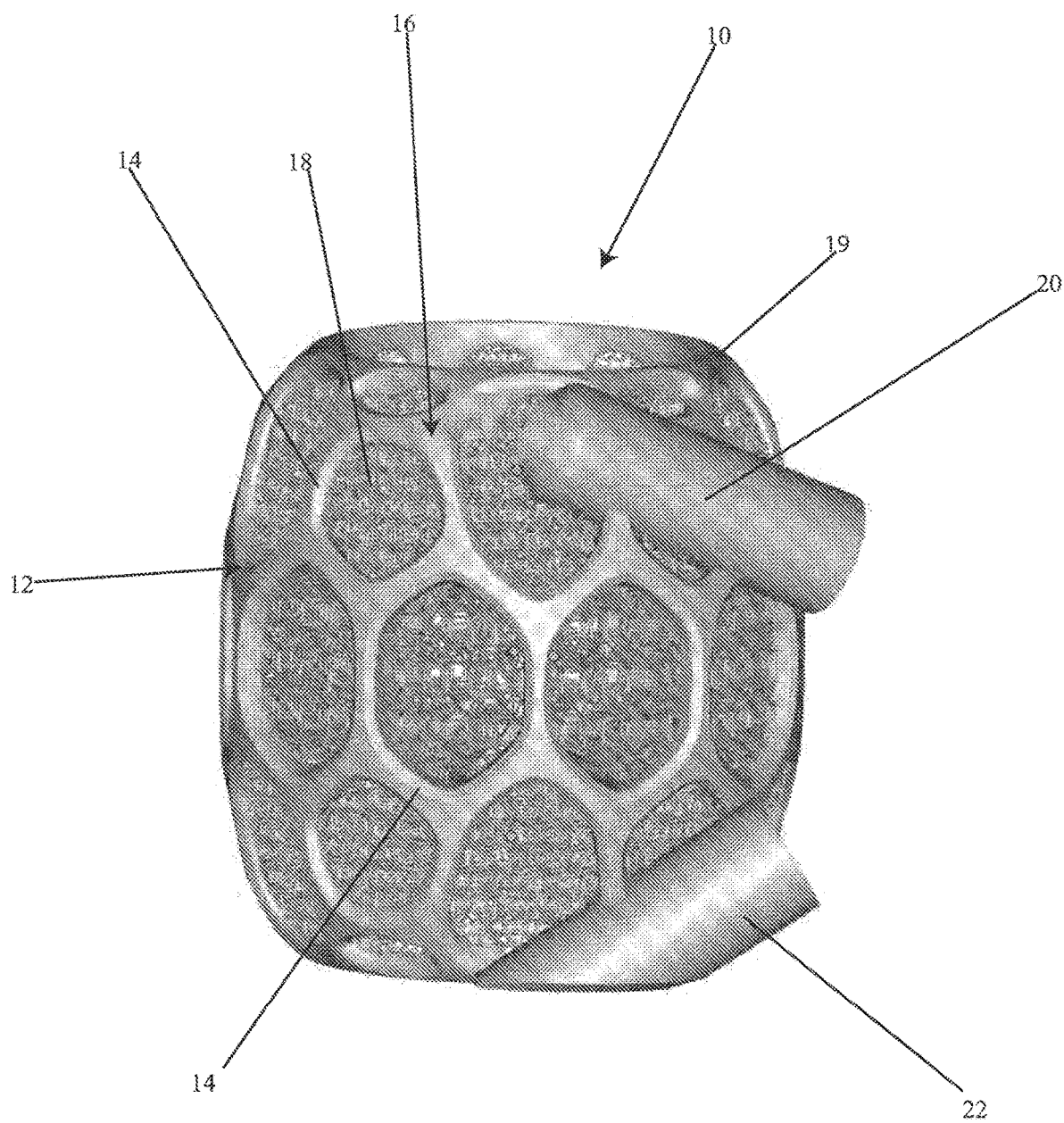
FIG. 1 is a side view of a first embodiment of a bone fixation device.

Referring to the drawings, FIG. 1 shows a side view of a first embodiment of a bone fixation device 10 which includes an outer shell/cage which comprises a plurality of struts 14. Struts 14 are configured to form a plurality of cells 16. Each of these cells can be shaped in a substantially hexagonal manner, however any suitable shape for each cell may be used. Each of the cells then joins another adjacent cell such that there are a plurality of cells forming an overall cage or shell having a honeycomb pattern. The cage 12 can be formed in any suitable shape but in this embodiment it is substantially spherical.

Figure 2A:
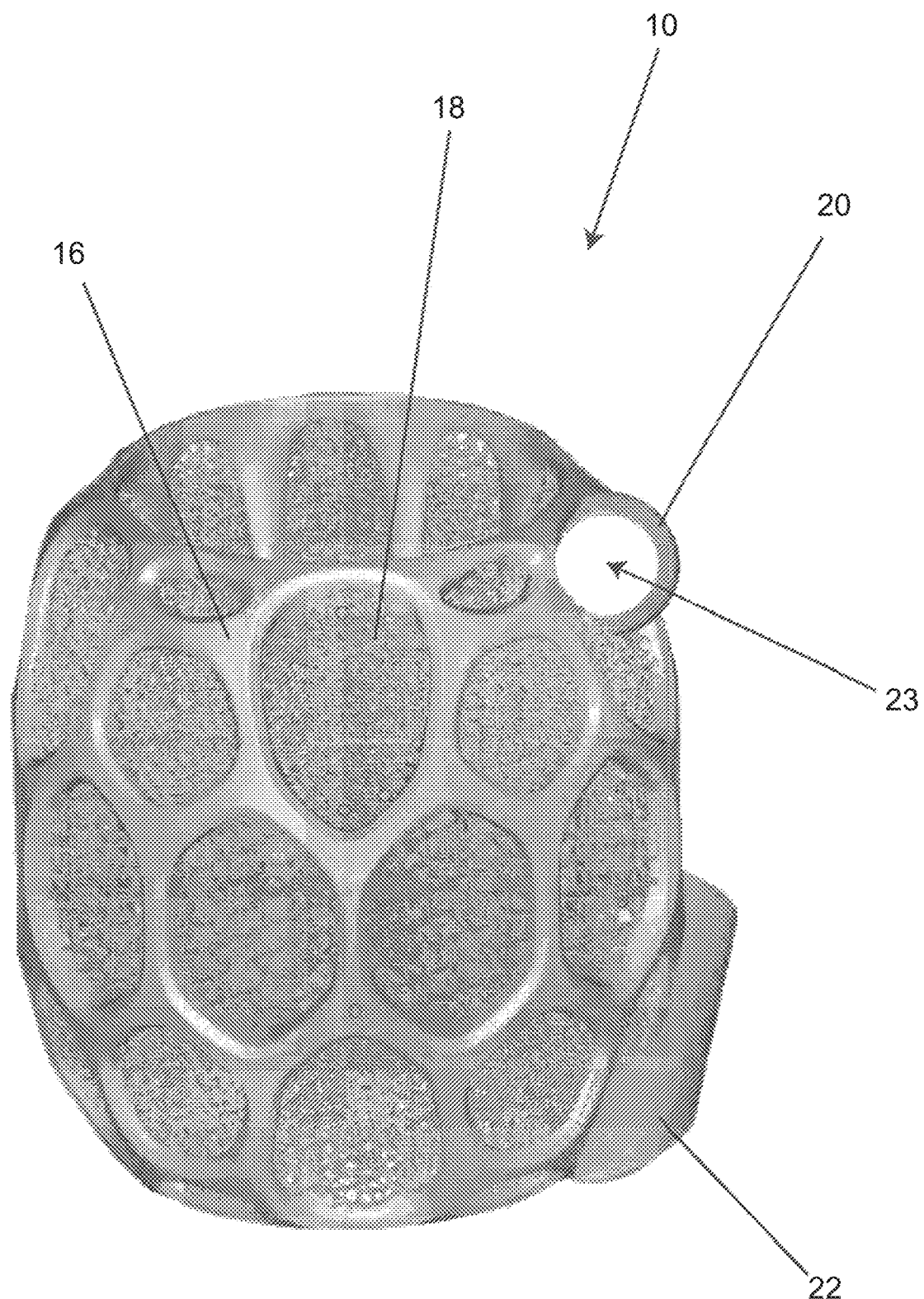
FIG. 2A is a perspective view of the embodiment shown in FIG. 1.

Disposed inside of the cage 12 is a mesh 18, which can be a mesh screen. The mesh screen can extend beyond the confines of the cage to mesh with adjacent bone. For example, the mesh screen can extend out beyond the cage by a pre-set margin such as 3 mm (millimeters) or at least 1 mm in one embodiment or at least 2 mm in another embodiment, to form an interactive surface radially outside of the surface of the struts of the cage 12. In at least one embodiment the mesh screen extends radially outside of the struts by no more than 5 mm. This radial extension is shown by way of example by arrow 18a extending out beyond the extension of the cage (See FIG. 2B, See also FIG. 9). In addition, the cage has an edge 19 which forms a rim (See FIG. 2C as well) which opens up into a post hole or central core 25. The bone fixation device can be formed as a two-piece device having a shell and a separate mesh screen or it can be formed as one piece and printed in a single printing process. Coupled to the cage 12 are a plurality of screw channels 20 and 22. Each of the screw channels 20 and 22 are configured as a hollow cylinder having a hollow core such as hollow core or hole 23 (See FIG. 2A) which is configured to receive a screw or other type of fastener.

Figure 2B:
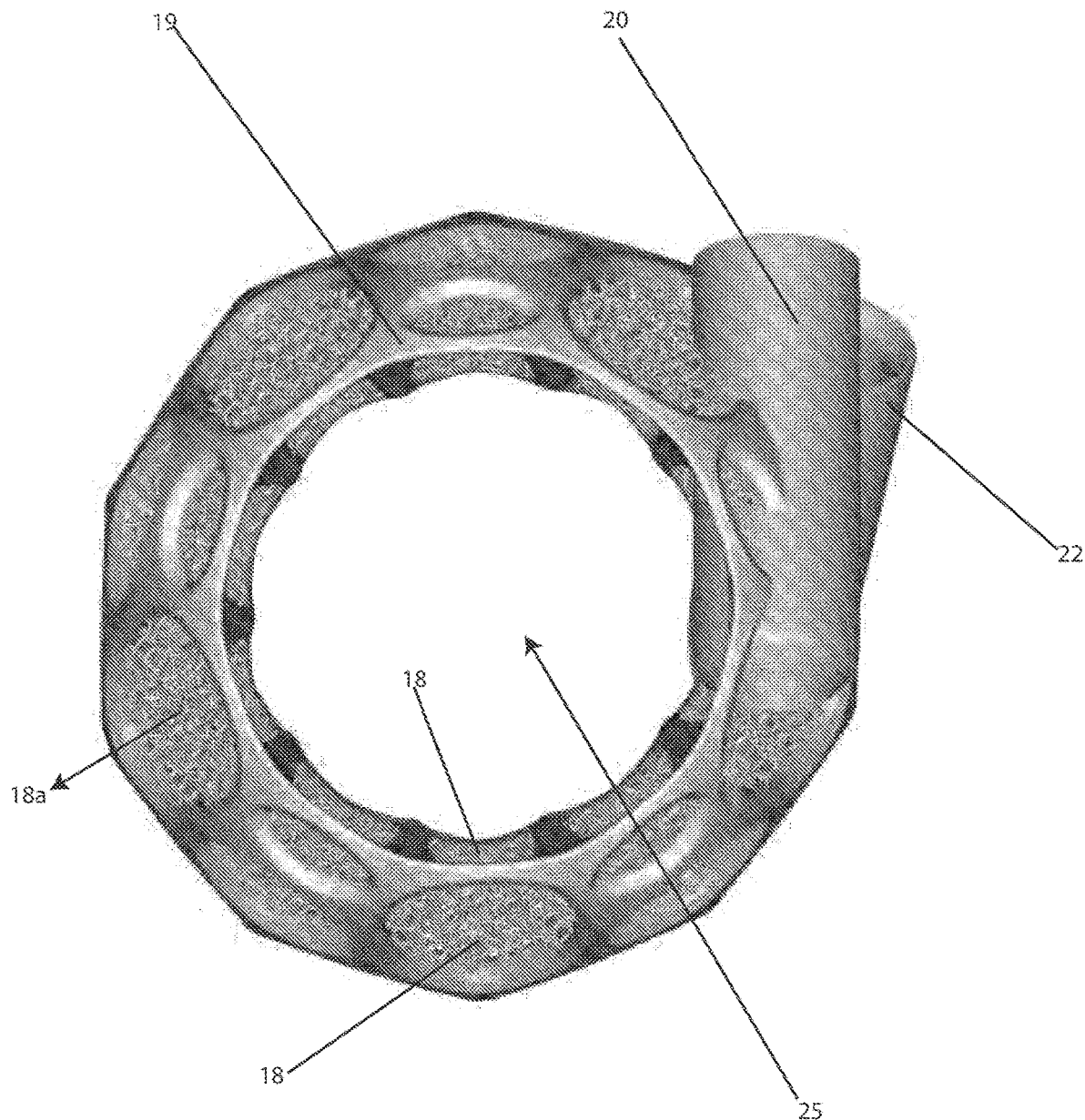
FIG. 2B is a top view of the embodiment shown in FIG. 1.

FIG. 2B is a top view of the embodiment shown in FIG. 1, in this view of the bone fixation device 10 is shown having a post hole or central hollow core 25 which is configured to allow a post to fit therein. The hollow core is formed to have a hollow core within the mesh portion as well. The mesh portion can have a varying lattice structure of varying density which is suitable to allow for selected bone growth rates. In addition, the mesh or lattice or mesh 18 is configured to receive bone growth material such as a gel or other type of bone growth material to aid in the growth in bone in the lattice.

Figure 3:
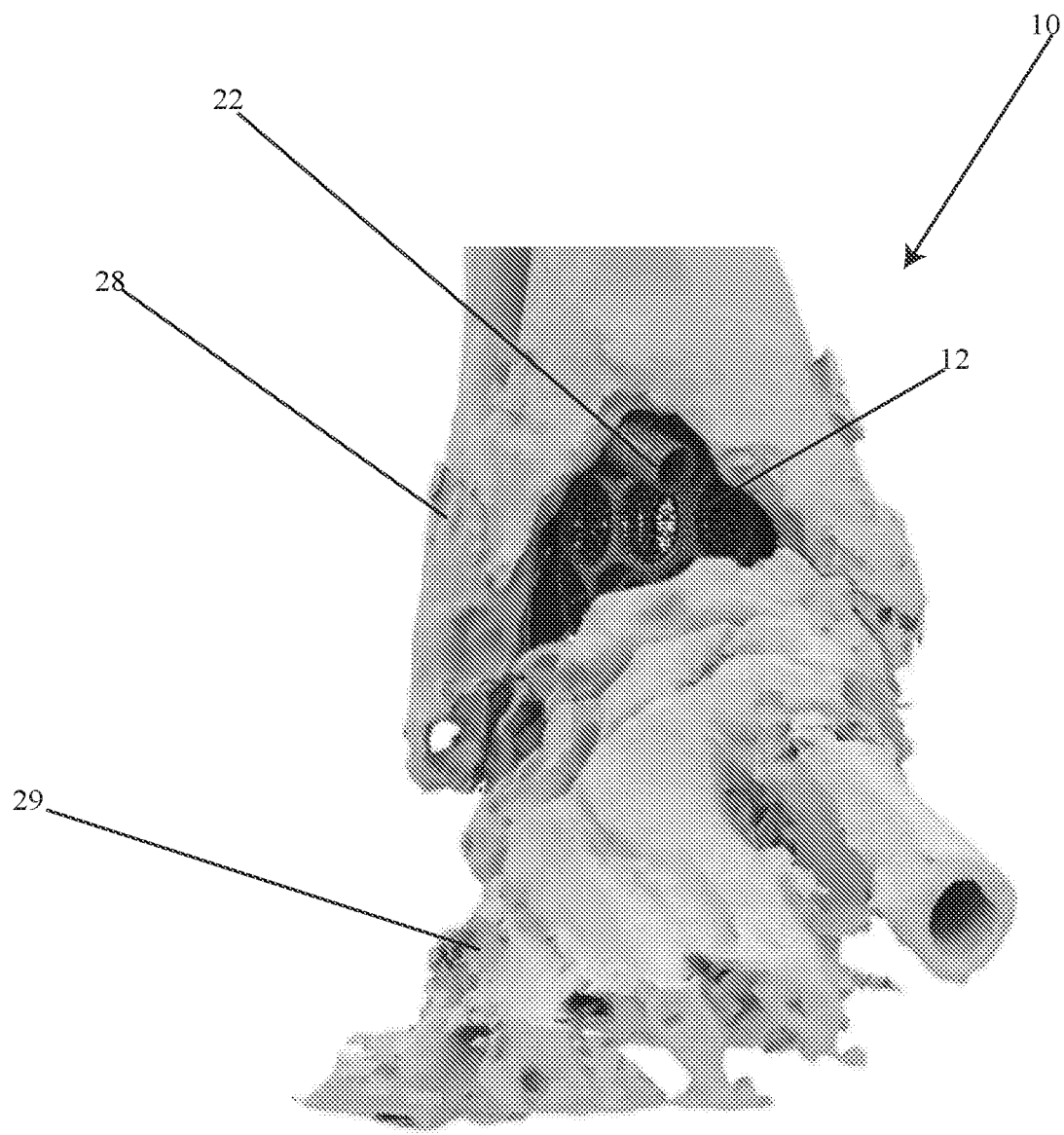
FIG. 3 shows a side view with this embodiment placed inside of an ankle joint.

FIG. 3 shows a side view with this embodiment of the device 10 placed inside of an ankle joint. This ankle joint includes a leg portion 28 and a foot portion 29, forming an ankle joint. This view shows cage 12 along with screw channel 22.

Figure 4:
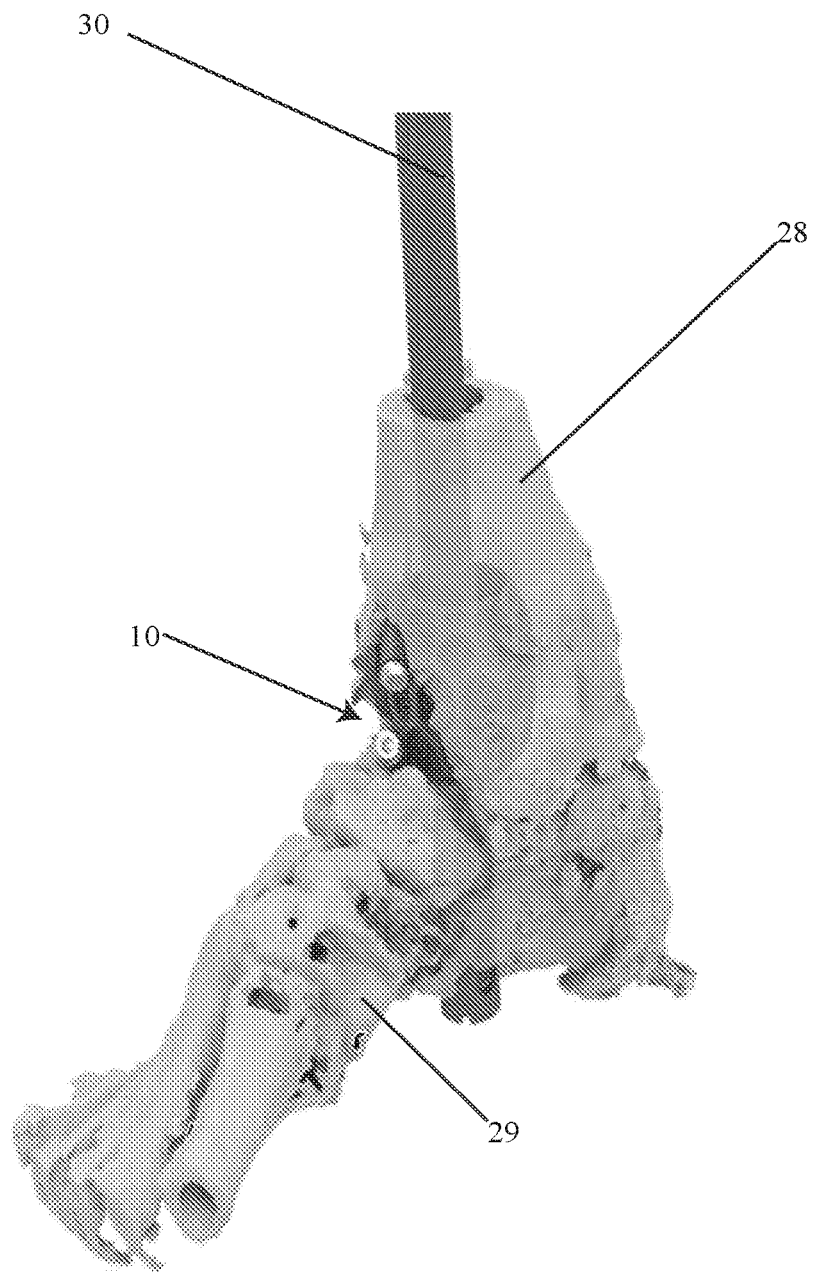
FIG. 4 is a side perspective view of another embodiment of the device placed inside of an ankle and including a post.

FIG. 4 is a side perspective view of the embodiment of the bone fixation device 10 having a post 30 disposed therein. With this design, post 30 comprises a shaft extending through the post hole or central core 25 (See FIG. 2B). Post 30 is configured to stabilize a tibia or leg portion of a person's leg.

Figure 5:
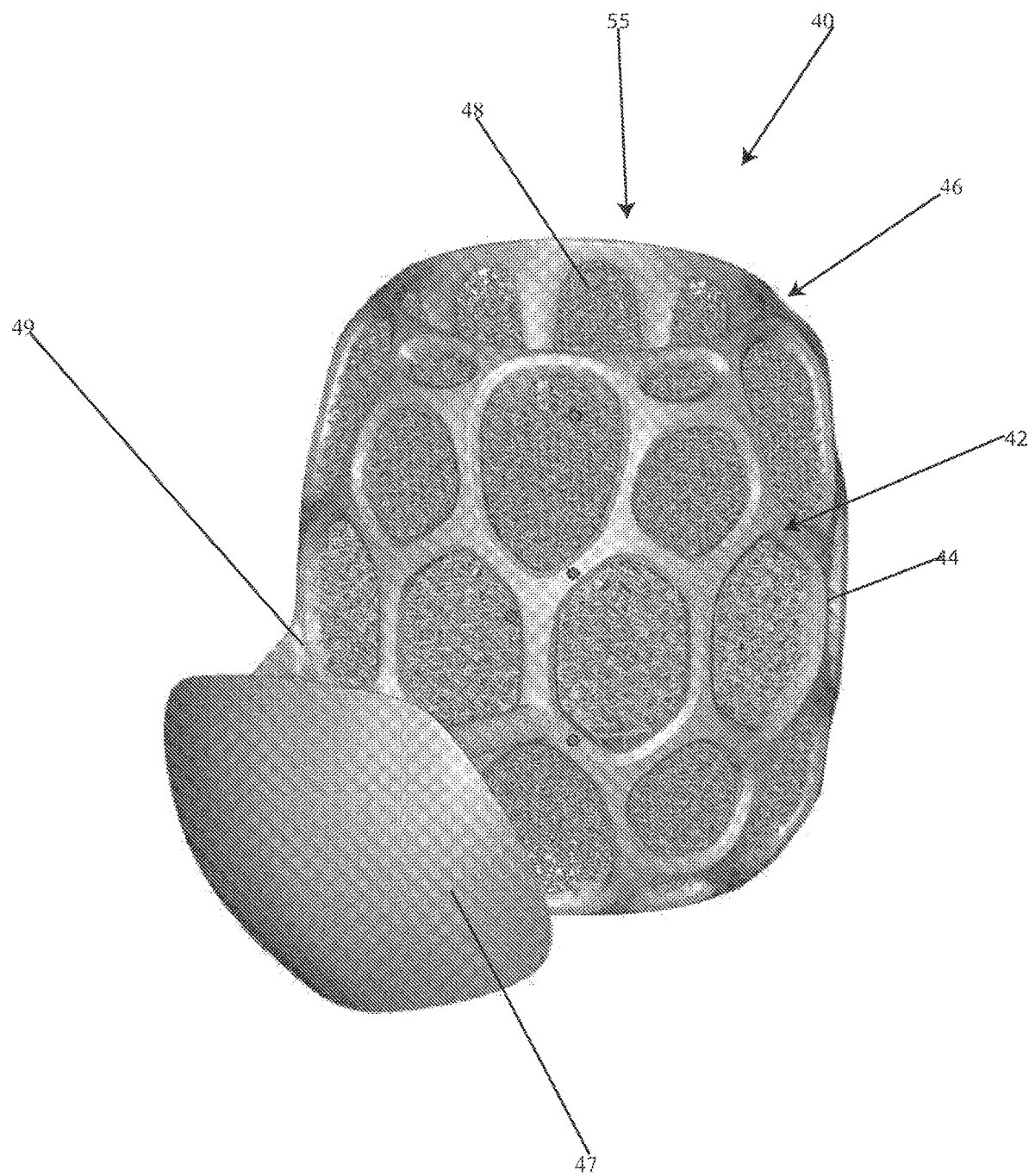
FIG. 5 is a side view of another embodiment.

FIG. 5 is a side view of another embodiment which is a bone fixation device 40 which includes a cage 42 having a plurality of struts 44, wherein a plurality of struts, such as six struts form a six-sided cell 46 which can be hexagonal in shape. There is also a plate 47 which extends out from cage 42 via an extension section 49. A mesh screen 48 is disposed in and around cage 42 and can be of a pre-set standard density or of a varying density as well. Thus, the density of the mesh screen can be that of a more dense structure in the middle with lower density at the exterior surfaces, a constant density throughout or a more dense structure on in the exterior surfaces with a less dense structure in the center. Alternatively, the density profile can vary from a more dense section towards a center hole (moving radially inwardly) such as center hole 55 to less dense on the outer edges (a radially outward region). Conversely the density profile can be that it is less dense on the outer edges both at the radially outward region and at the center region (adjacent to the center hole) towards a more dense profile towards a center region of the body between the radially outward region and the center hole. Alternatively, the density profile can be such that it is most dense towards the radially outward region and least dense at the center hole 55. These same density profiles can apply with any of the embodiments disclosed herein.

Figure 6:
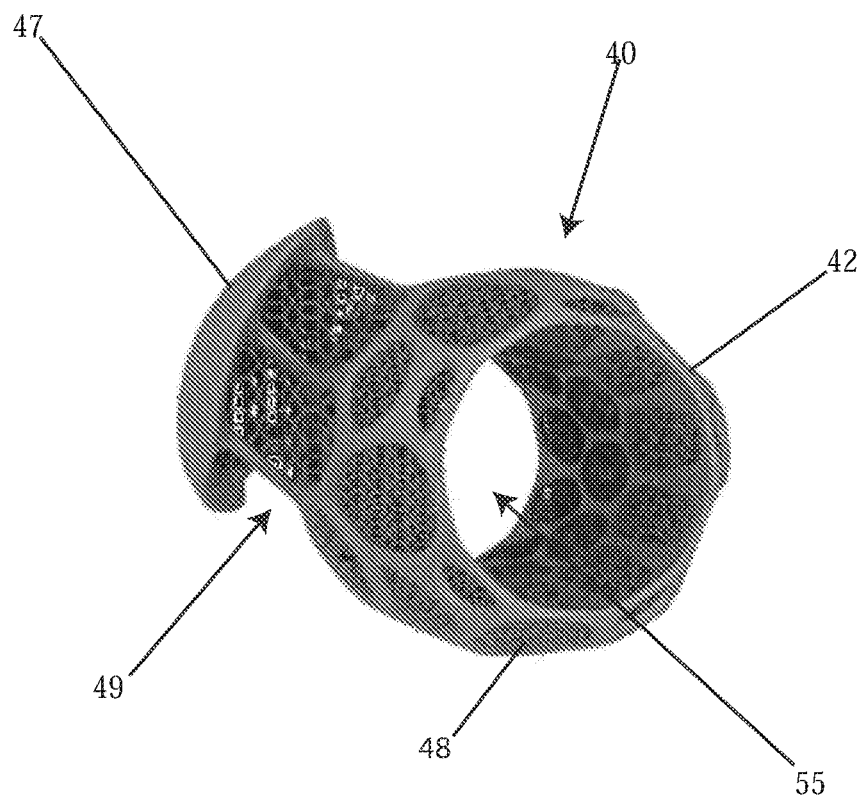
FIG. 6 is a top perspective view of another embodiment.

FIG. 6 is a top perspective view of the second embodiment wherein this shows the device 40 having an extension section 49 extending to plate 47. The cage 42 also has a central post hole 55 configured to receive a post inserted therein. With this design as well the mesh screen is configured to extend radially beyond the surface of a cage such as cage 42 to provide additional surface interaction with a surrounding bone.

Figure 7:
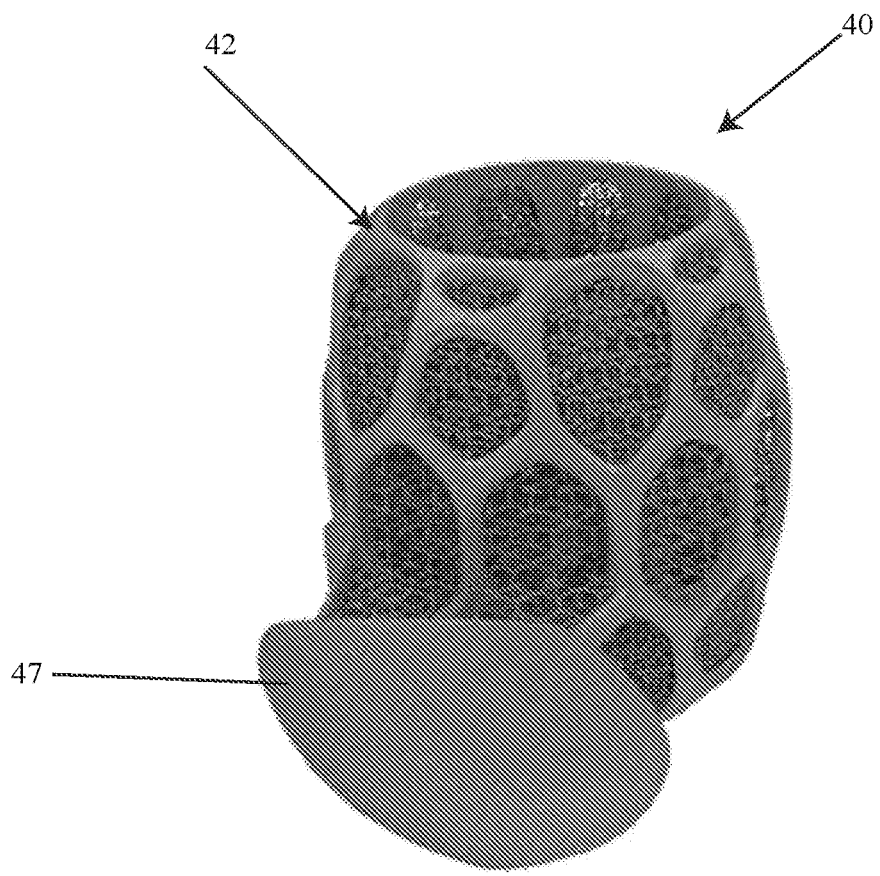
FIG. 7 is a side-top perspective view of the second embodiment.

FIG. 7 is a side-top perspective view of the device 40 showing plate 47 extending from cage 42. Plate 47 is configured to be an irregular shaped plate with a rounded exterior plate surface. In at least one embodiment this plate shape is at least substantially semi-spherical in shape.

Figure 8:
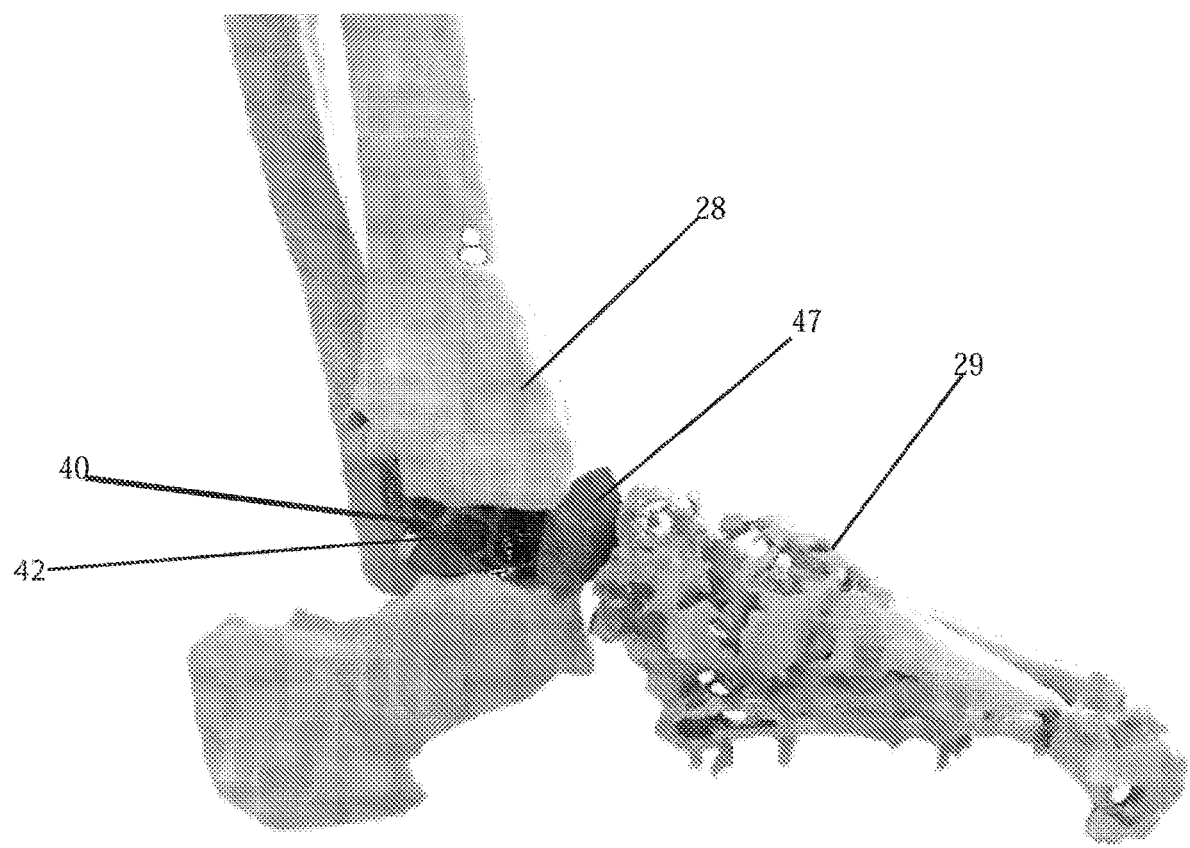
FIG. 8 is a top-side perspective view of the second embodiment.

FIG. 8 is a top-side perspective view of the device embedded inside of a leg section 28 and a foot section 29 with plate 47 extending from cage 42 and bracing against foot 29.

Figure 9:
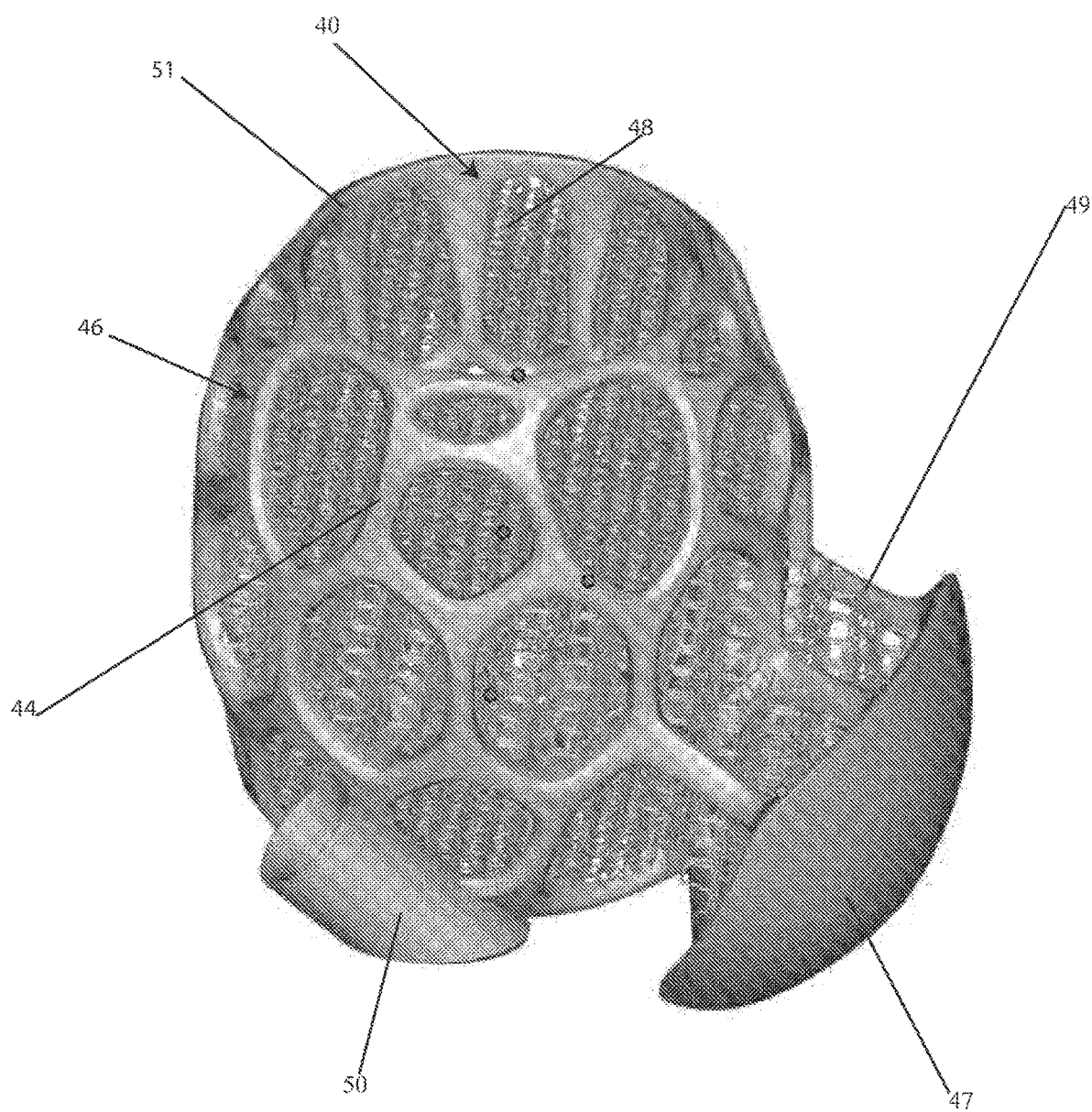
FIG. 9 is a another side-top perspective view of the second embodiment.

FIG. 9 is another side-top perspective view of the device 40 which shows another view of the extension section 49, with plate 47 being shown a substantially rounded in a dome like or semi-spherical shape. A screw channel 50 is also shown having a screw hole. There is shown also struts 44 of cage 42 with the struts forming cells 46. An upper rim 51 is formed to provide for a central post hole 55 (see FIG. 6). As shown, the mesh screen or lattice 48 extends beyond the frame or struts 44 of cage 42.

Figure 10:
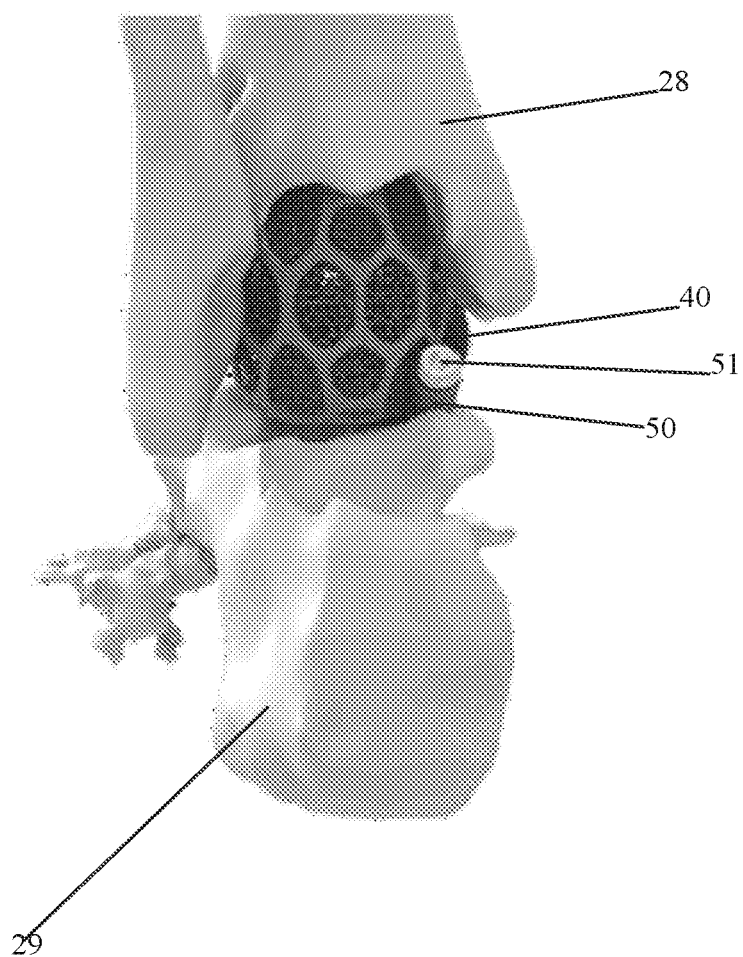
FIG. 10 is an end view of a foot with the second embodiment disposed in the ankle joint.

FIG. 10 is an end view of a foot with the device 40 disposed in the ankle joint which is formed by the leg section 28 and the foot section 29. There is also shown a screw channel 50 as well as a fastener such as a screw 51 inserted therein. While the device 40 or device 10 can be fastened to an adjacent bone using known fasteners, other types of fasteners can be inserted into a bone so that the cage 12 or 42 is secured or friction fit into the bone and then this allows the device to be adhered to a bone such as a tibia, a foot, a toe or any other end or terminating bone structure. Thus, this design allows for one of many different types of fixation such as a friction fit (FIG. 22), a screw for fixation (FIG. 3, 4, or 8), or a plate for fixation (See FIG. 27).

Figure 11:
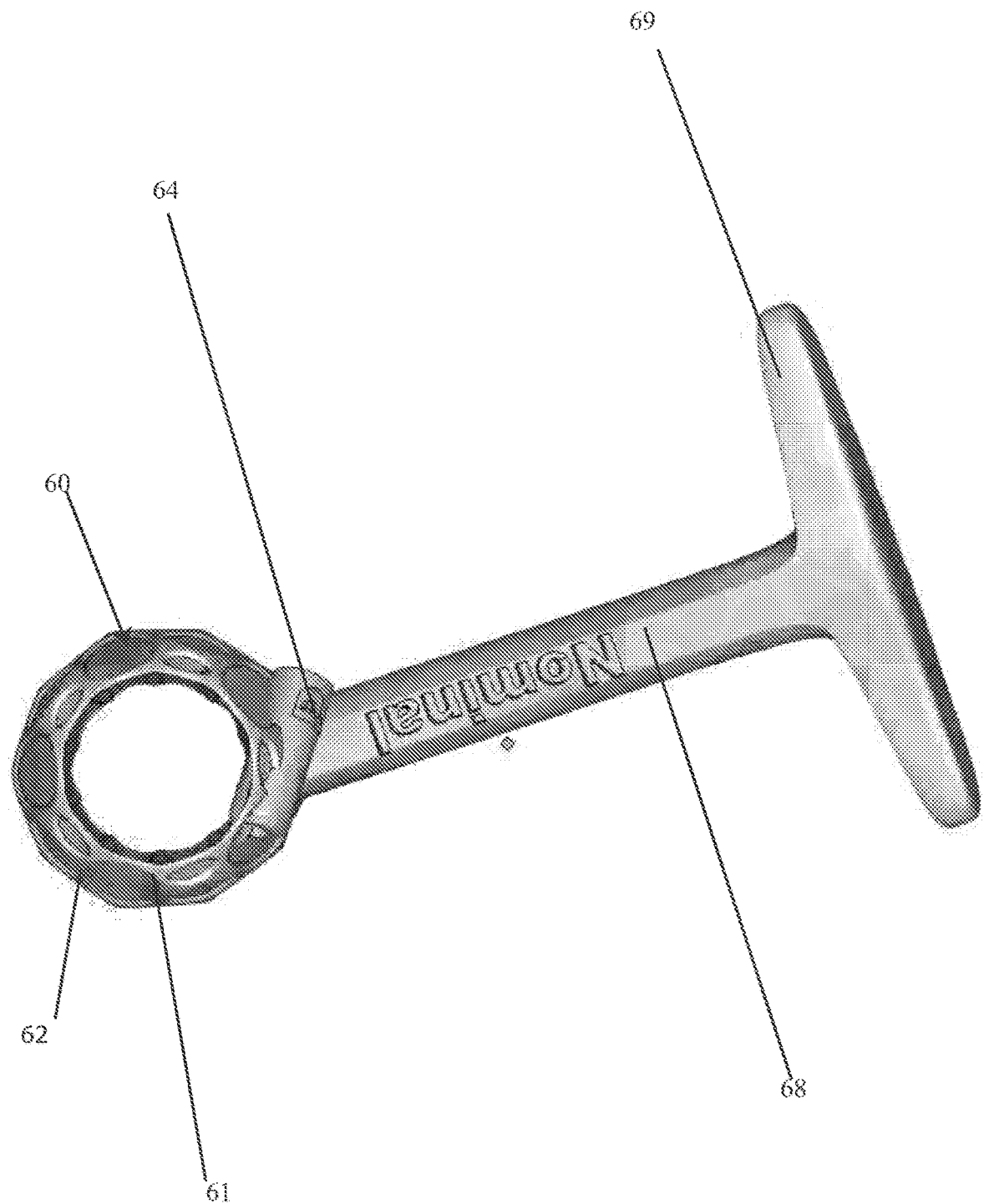
FIG. 11 is a plan view of a third embodiment.

FIG. 11 is a plan view of a third embodiment which shows a bone fixation device 60 having a body section 61 having a cage 62. There is also a screw channel 64 coupled to body section 61 as well. Coupled to body section 61 is at least one elongated shaft 68. Coupled to the elongated shaft 68 is at least one T section 69. T section 69 extends substantially perpendicular to elongated section 68. T-section and elongated shaft form a handle for allowing for the trial insertion of the bone fixation device 10 or 40 into the patient's leg.

Figure 12:
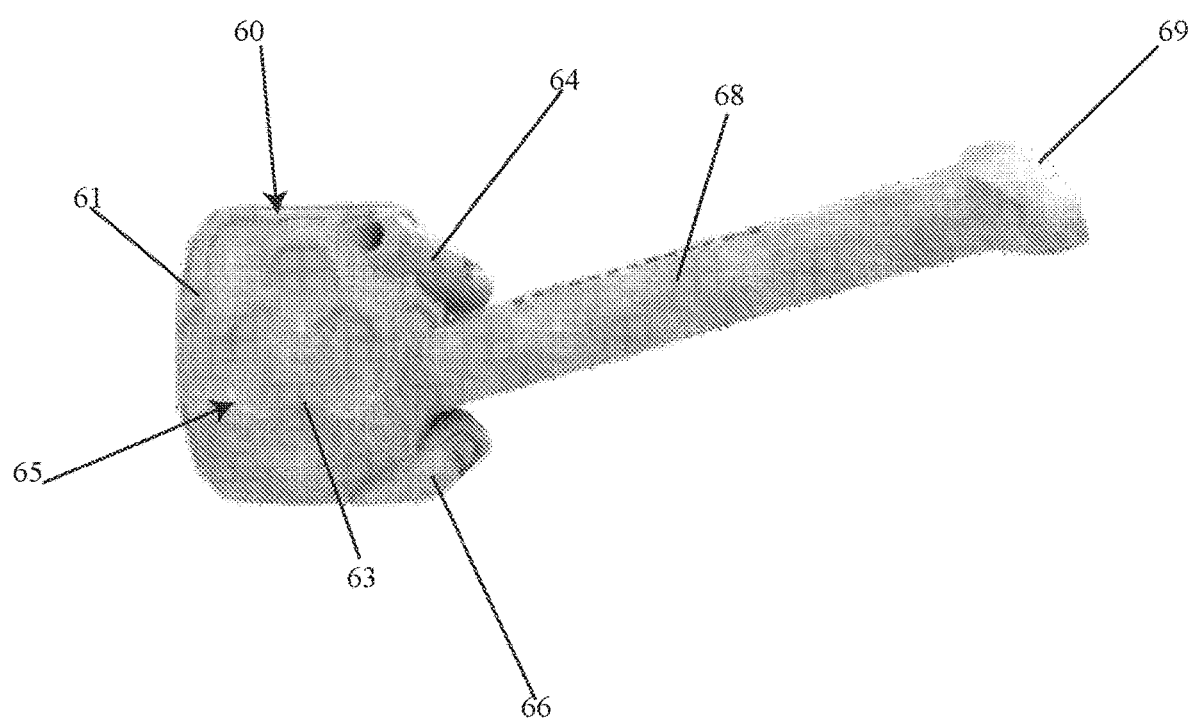
FIG. 12 is a side view of the third embodiment.

FIG. 12 is a side view of device 60 which shows a body section 61 having a plurality of struts 63 forming cells 65. A second screw channel 66 is also coupled to body section 61. Each of these screw channels are configured to receive a fastener such as a screw such that the body section can be fastened to an adjacent structure such as a bone.

Figure 13:
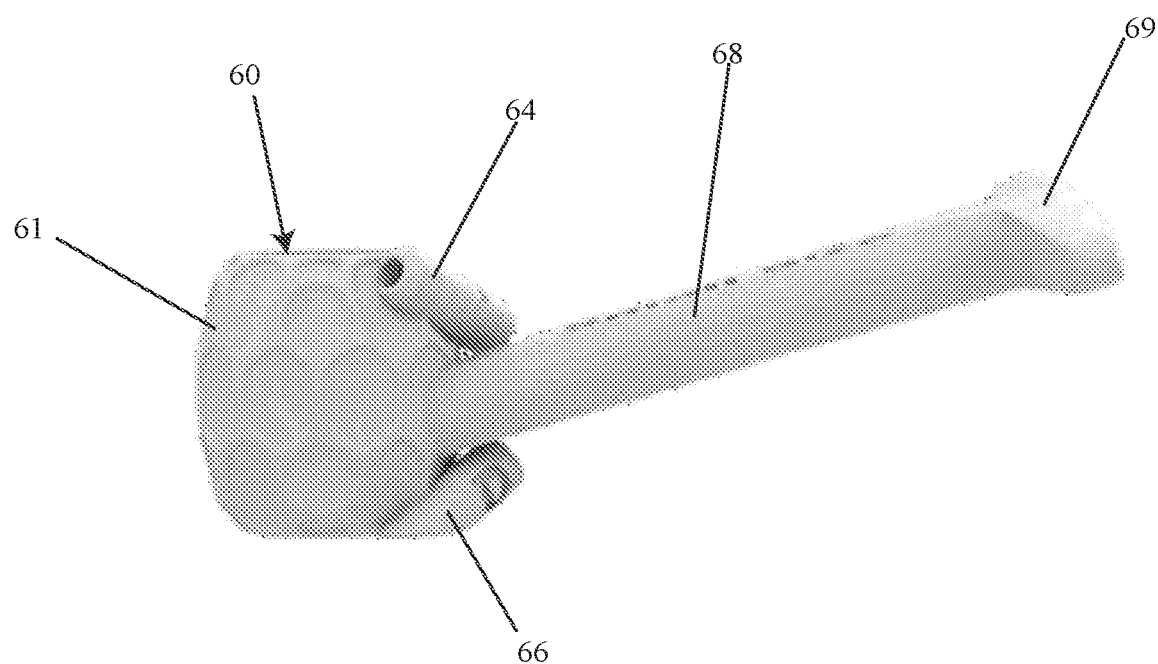
FIG. 13 is a side view of the third embodiment.

FIG. 13 shows another view of this embodiment or device 60 showing body section 61, screw channels 64 and 66 along with elongated sections 68 and T section 69.

Figure 14:
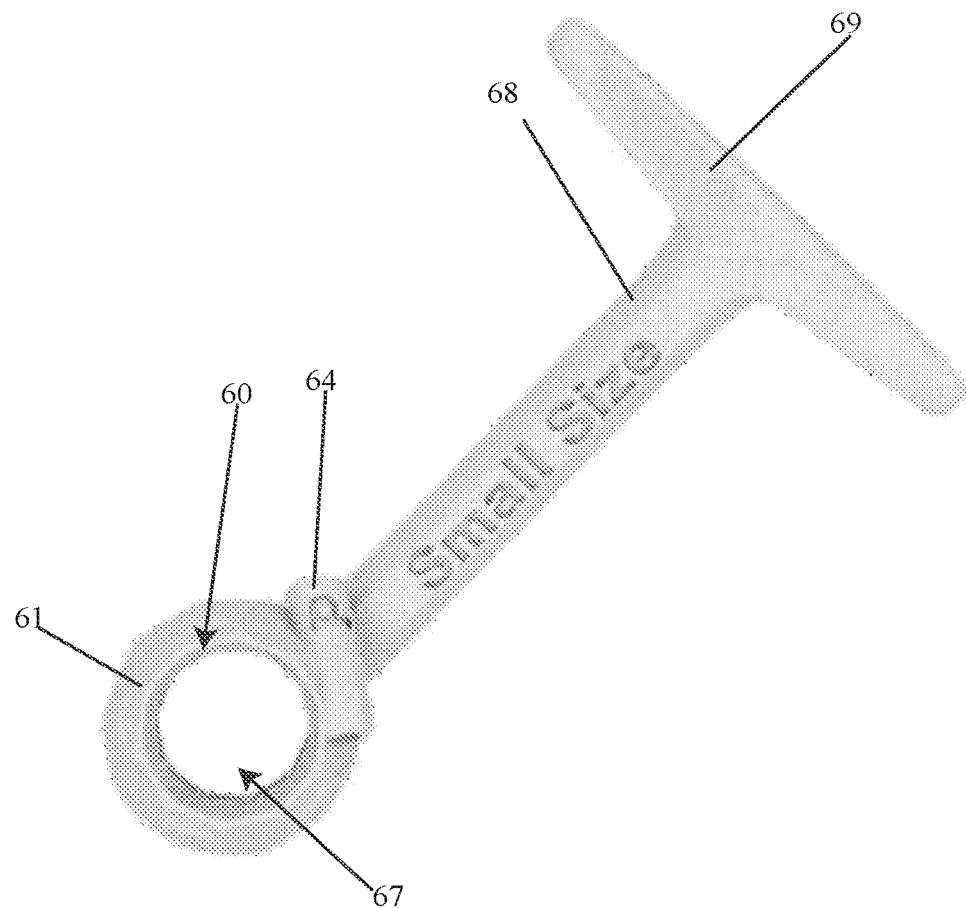
FIG. 14 is a top plan view of a fourth embodiment.

FIG. 14 shows a top view of device 60 which shows body section 61, screw channel 64, elongated shaft 68 and T section 69. A central post hole 67 is also shown which allows a post to be inserted therein.

Figure 15:
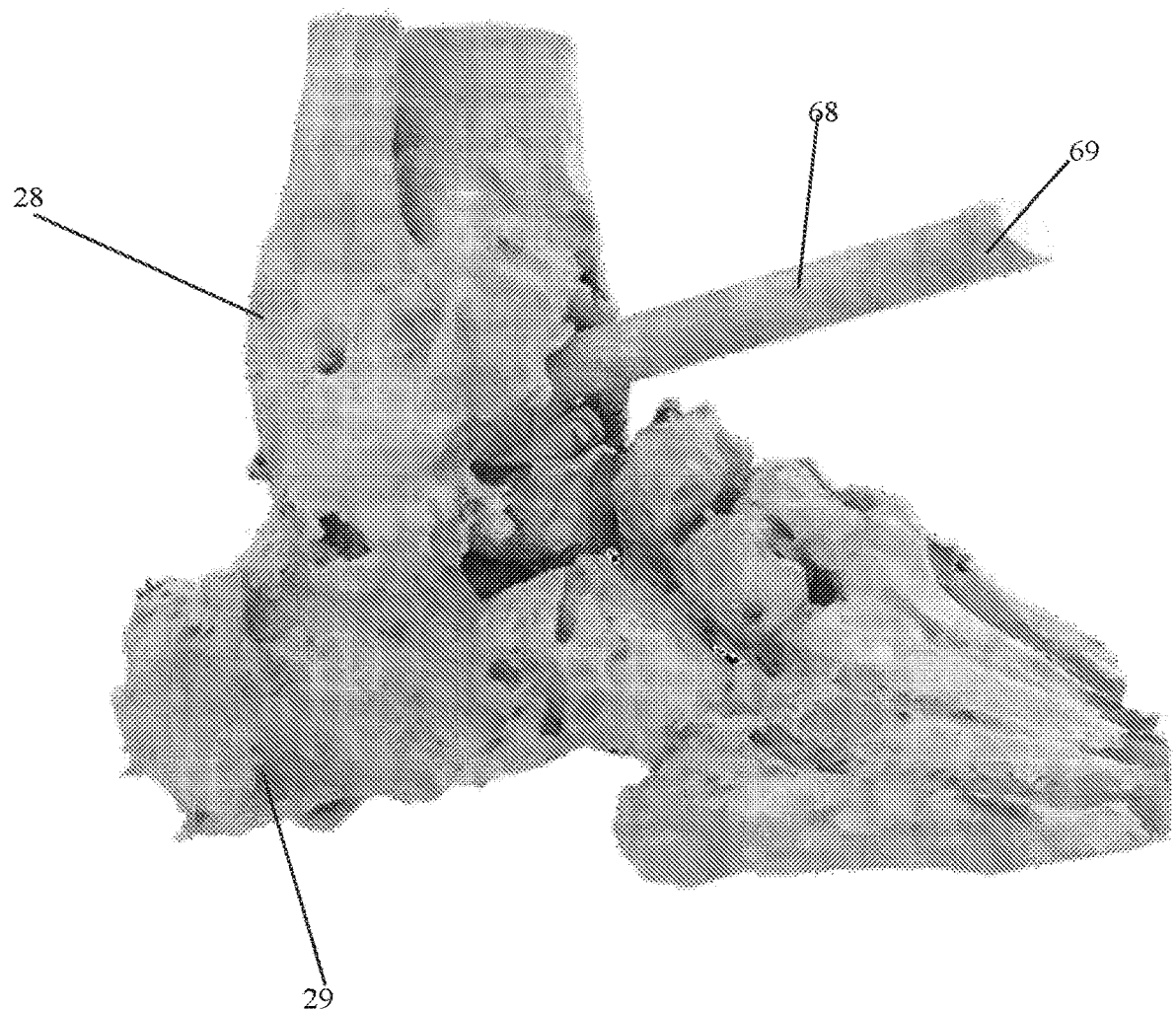
FIG. 15 is a side view of either a third or fourth embodiment disposed in an ankle region.

FIG. 15 shows this embodiment inserted into an ankle region wherein it is disposed between a leg portion 28 and a foot portion 29. Elongated shaft 68 is shown extending out from this ankle section to T section 69.

Figure 16:
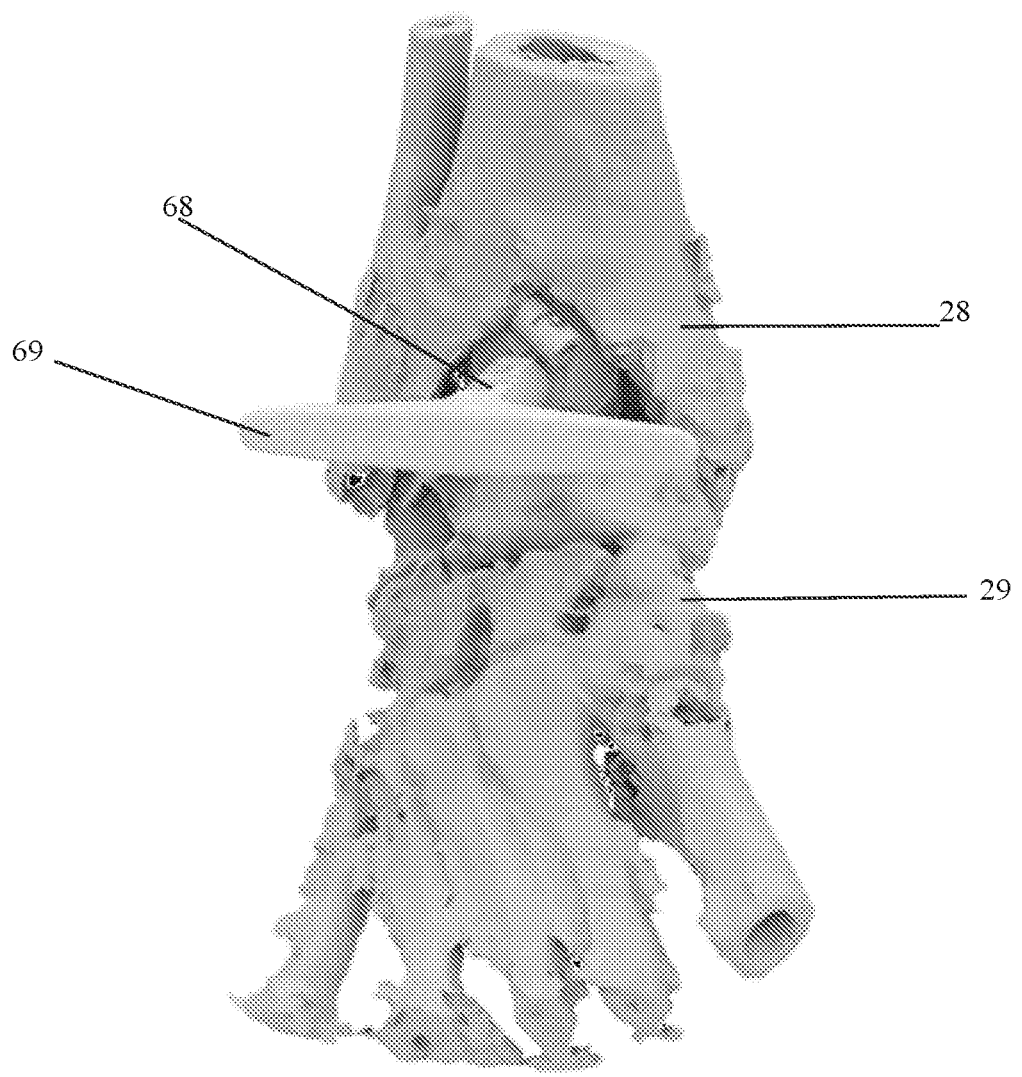
FIG. 16 is another view of the third or fourth embodiment disposed in a person's ankle.

FIG. 16 is another view of the third or fourth embodiment showing device 60 disposed in a person's ankle with extension section or elongated shaft 68 extending out to T section 69 which extends over a person's foot 29 and out in front of a person's leg 28.

Figure 17:
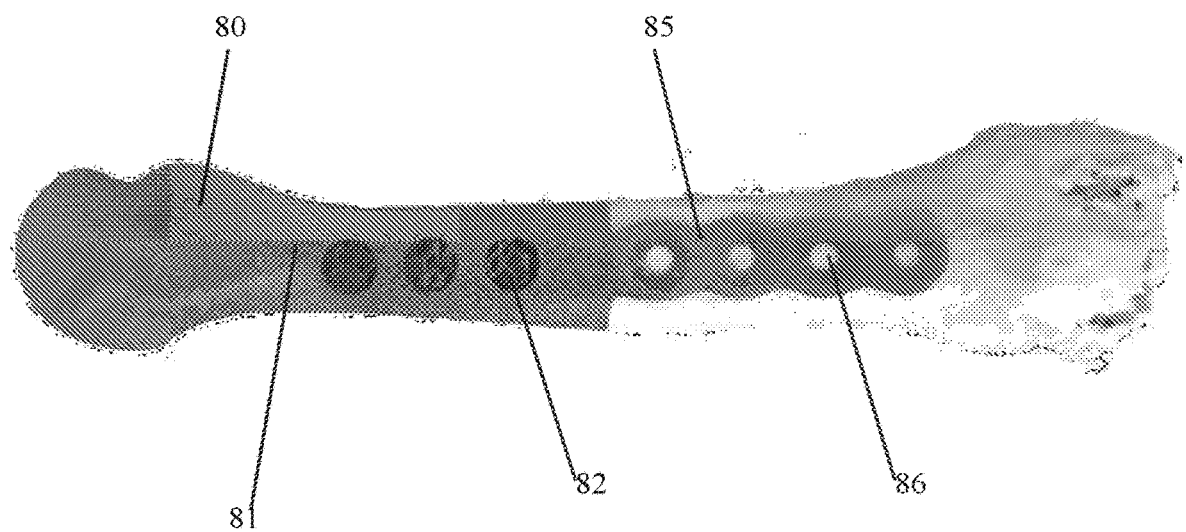
FIG. 17 is a view of a fifth embodiment coupled to a bone.

FIG. 17 is a view of a fifth embodiment of a bone fixation device 80 coupled to a bone such as a leg bone 28. This embodiment includes a body section 81 which can have any shape but in at least one embodiment has a substantially cylindrical shape with a substantially spherical end cap. This body section 81 having a plurality of screw holes 82 disposed therein. There is an extending portion 85 which also includes a plurality of screw holes 86 as well. Body section is formed to fit over the end of a leg portion such as a tibia bone of a leg.

Figure 18:
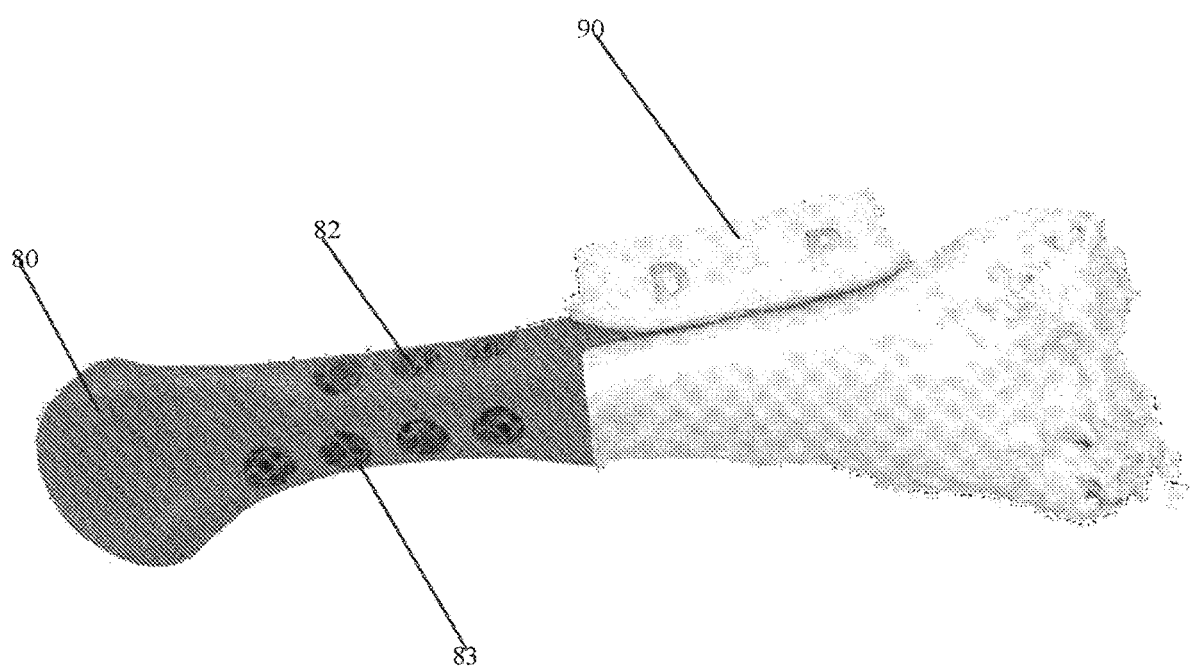
FIG. 18 is another view of the fifth embodiment coupled to a bone.

FIG. 18 is another view of the bone fixation device 80 coupled to a bone such as a tibia bone. In this embodiment, drill guide 90 is configured to guide screws or drill holes other fasteners as they are drilled into bone to fix the an implant to the bone. As shown in this view guide fixation device 80 includes drill holes 82 and 83 as well. Thus, the drill guide 90 is configured to guide a user in inserting screws into the drill holes 82 and 83 respectively.

Figure 19:
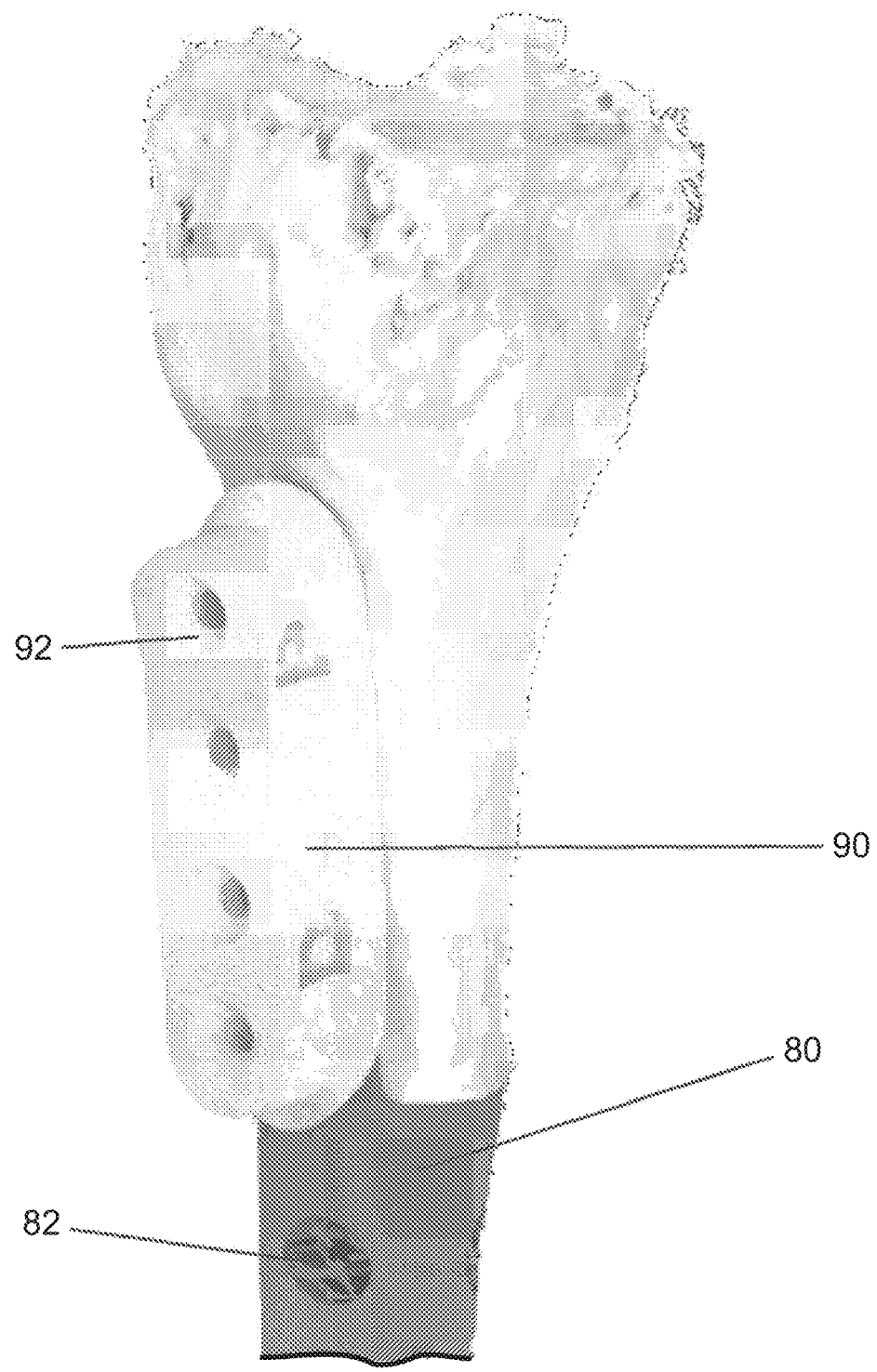
FIG. 19 is a side view of the fifth embodiment.

FIG. 19 is a side view of the fifth embodiment showing bone fixation device 80 having drill guide 90 which has a plurality of drill holes 92 disposed therein. In addition, as shown in this view there is a drill hole 82 which is visible as well. For example, drill holes 92 can be configured to line up with drill holes 82 so that guide 90 forms a guide for inserting fasteners such as screws to couple fixation device 80 to a person's leg.

Figure 20:
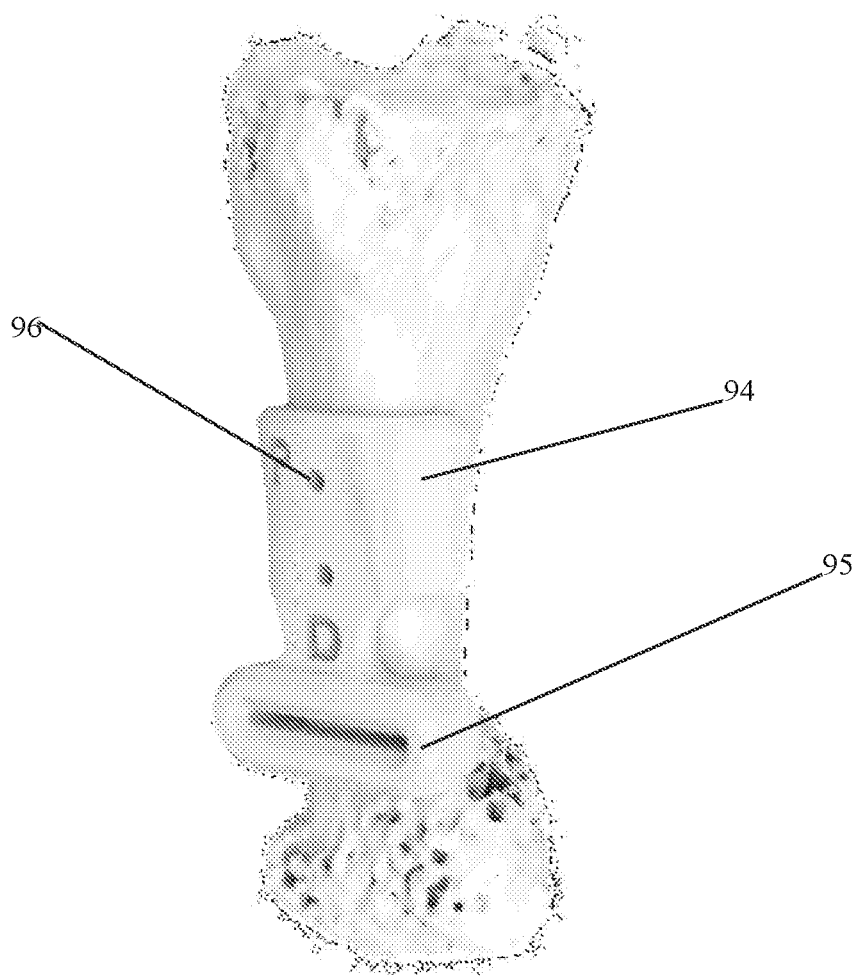
FIG. 20 is a top perspective view of the fifth embodiment

FIG. 20 is a top perspective view of a cut guide 94 which has a proximal end labeled "P" and a distal end labeled "D" with a plurality of drill holes 96 disposed therein. There is also a slot 95 disposed adjacent to the distal end. The cut guide provides a guide for a doctor or surgeon to cut a person's bone. This cut guide 94, the drill guide 90 and an associated bone fixation device such as bone fixation device 80 can be assembled in a kit such as a surgical kit for performing a coupling of the bone fixation device to a person's bone.

Figure 21:
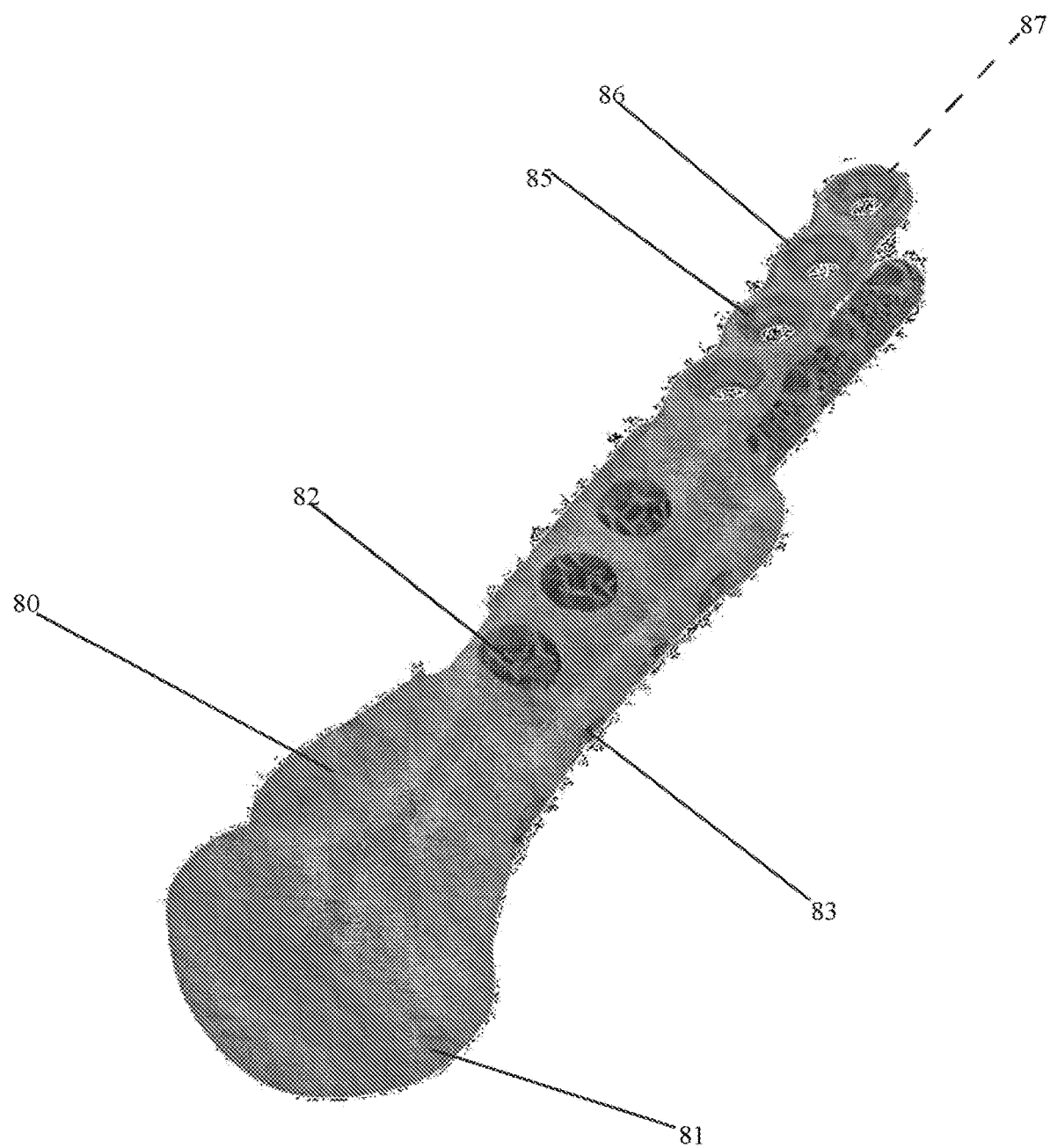
FIG. 21 is a side view of the fifth embodiment.

FIG. 21 is a side view of the device 80 which shows a body section 81, drill holes 82, and 83 as well as an elongated section 85 having at least one drill hole 86. The elongated section 85 extends along longitudinal axis 87 to create an elongated body of the device 80. The device is configured to form an end cap on then end of a person's bone. This end cap can have a substantially spherical surface signifying the end structure of a bone.

Figure 22:
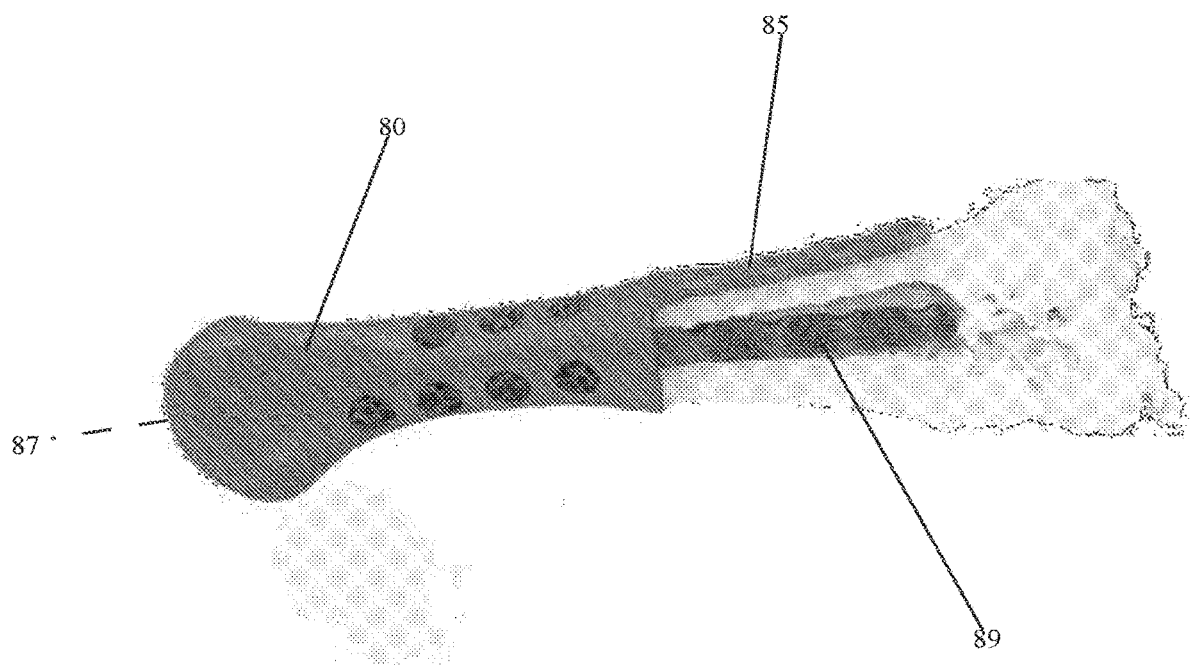
FIG. 22 is a side view of a sixth embodiment.

FIG. 22 is a side view of the device 80 which includes two elongated sections 85 and 89 which extend substantially along longitudinal axis 87. Each of these elongated sections has drill holes to allow the device to be secured to a user's bone. While elongated section 85 can be screwed into the bone, elongated section 89 can be inserted into a bone so that it is friction fit into the bone and then this allows the device to be adhered to a bone such as a tibia, a toe or any other end or terminating bone structure. In at least one embodiment, the elongated member inserts into a center of the bone. It can be pushed into the center of the bone canal like a hip stem. The other elongated plate 85 sits on top of the bone. Screws or other fasteners are inserted through the holes 86 through the bone and then into the matched holes on elongated section 89. The drill guide 90 shown in FIG. 19 allows for drilling in fasteners into holes 92 so that the fasteners match the holes 86 on elongated section 85 with the holes on elongated section 89 to fasten the device to an adjacent bone. Thus, this design allows for one of many different types of fixation such as a friction fit (FIG. 22), a screw for fixation (FIG. 3, 4, or 8), or a plate for fixation (See FIG. 27).

Figure 23:
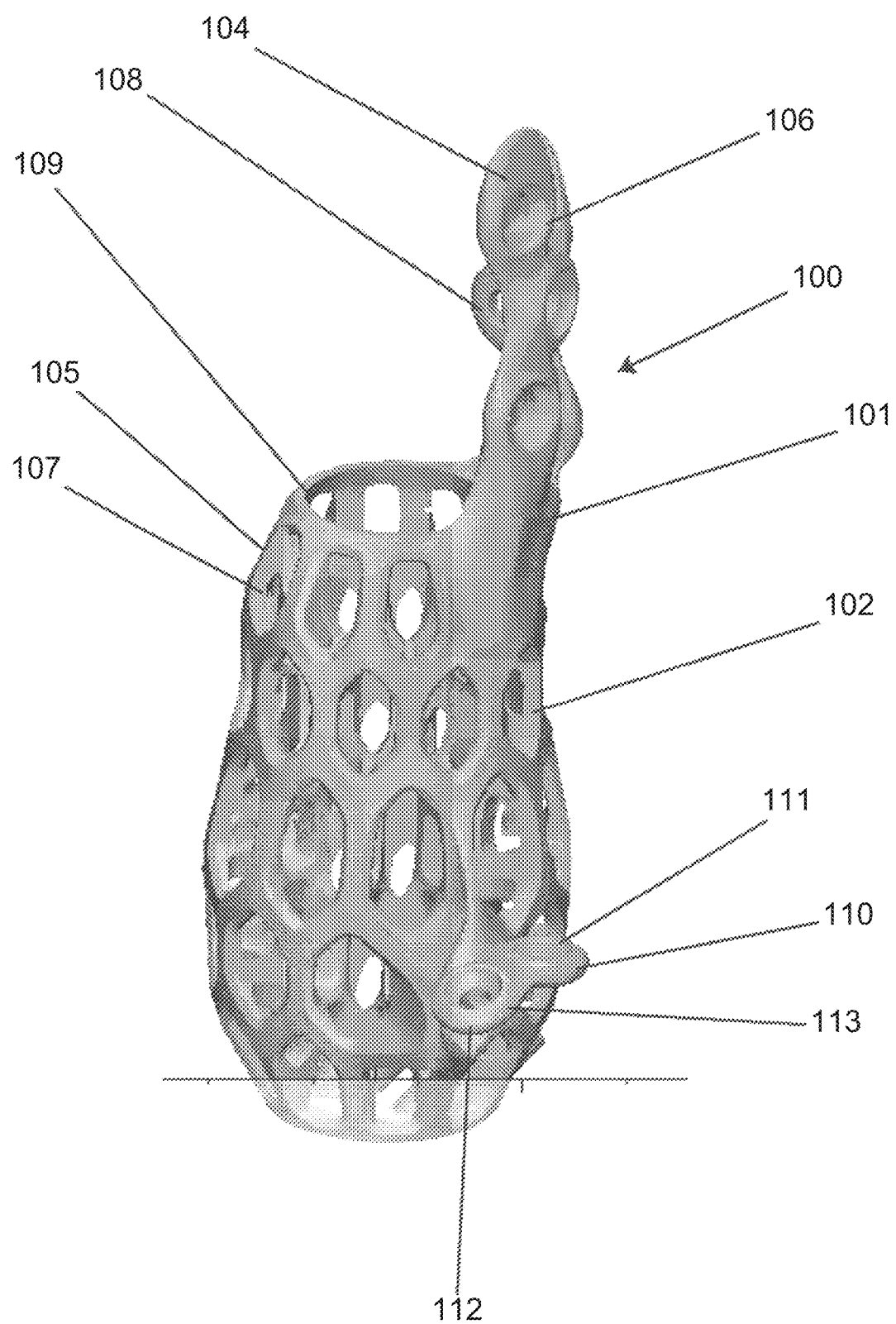
FIG. 23 is a side view of a seventh embodiment.

FIG. 23 is a side perspective view of another embodiment which includes a cage device 100 having a body section 101. A plurality of holes 102 are formed in body section 101. In addition, there are a plurality of elongated sections 104 and 108, wherein each of these elongated sections has holes such as holes 106. The body section 101 includes a plurality of struts 105 which each form cells 107. The cells can be of any suitable shape but in this case can be hexagonal in shape. Body section 101 is substantially rounded and in this case is substantially pear shaped. A plurality of protruding sections including protruding section 110 and protruding section 112 extend out laterally from body section 101 in a substantially transverse manner. Each of these protruding sections 110 and 112 has a respective hole 111 and 113. Each of holes 111 and 113 is configured to receive a fastener such as a screw.

Figure 24:
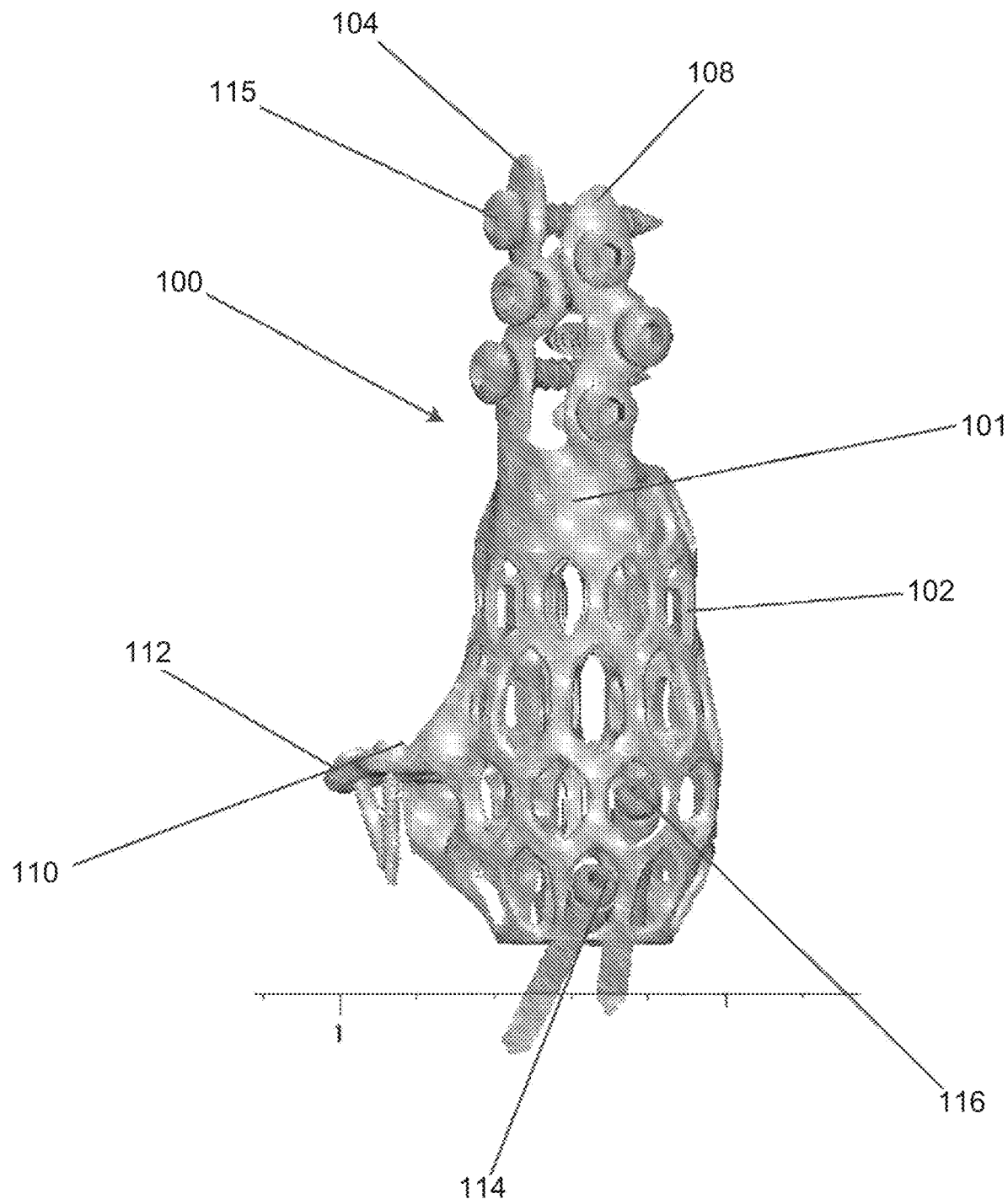
FIG. 24 is a side view of the seventh embodiment having fasteners.

FIG. 24 shows a view of the device 100 including a plurality of fasteners 115. There is shown extending sections 104 and 108 each configured to receive fasteners such as fasteners 115, while body section 101 has holes 102 as well as protruding fastening sections 110 and 112 configured to receive fasteners extending in a manner substantially parallel to the longitudinal extension of the body section 101. Fastening sections 110 and 112 extend out laterally from the body section 101.

A plurality of screw channels 114 and 116 are shown disposed in the body section 101 as well.

Figure 25:
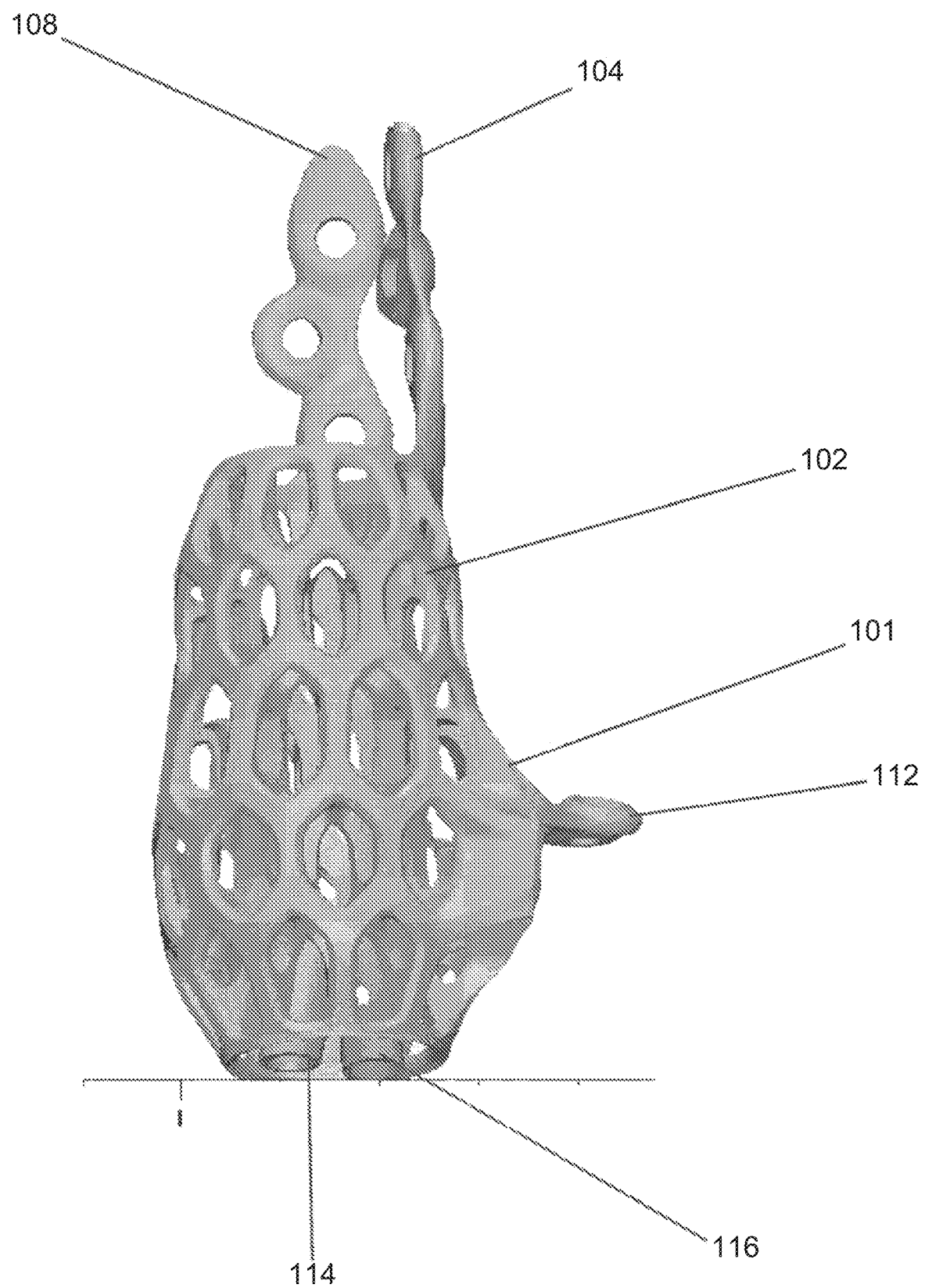
FIG. 25 is another side view of the seventh embodiment.

FIG. 25 shows another view of the embodiment 100 which shows body section 101 with a protruding fastening section 112 extending out therefrom. Elongated sections 104 and 108 are shown extending out therefrom as well. Disposed in body section 101 are holes 102 as well.

Figure 26:
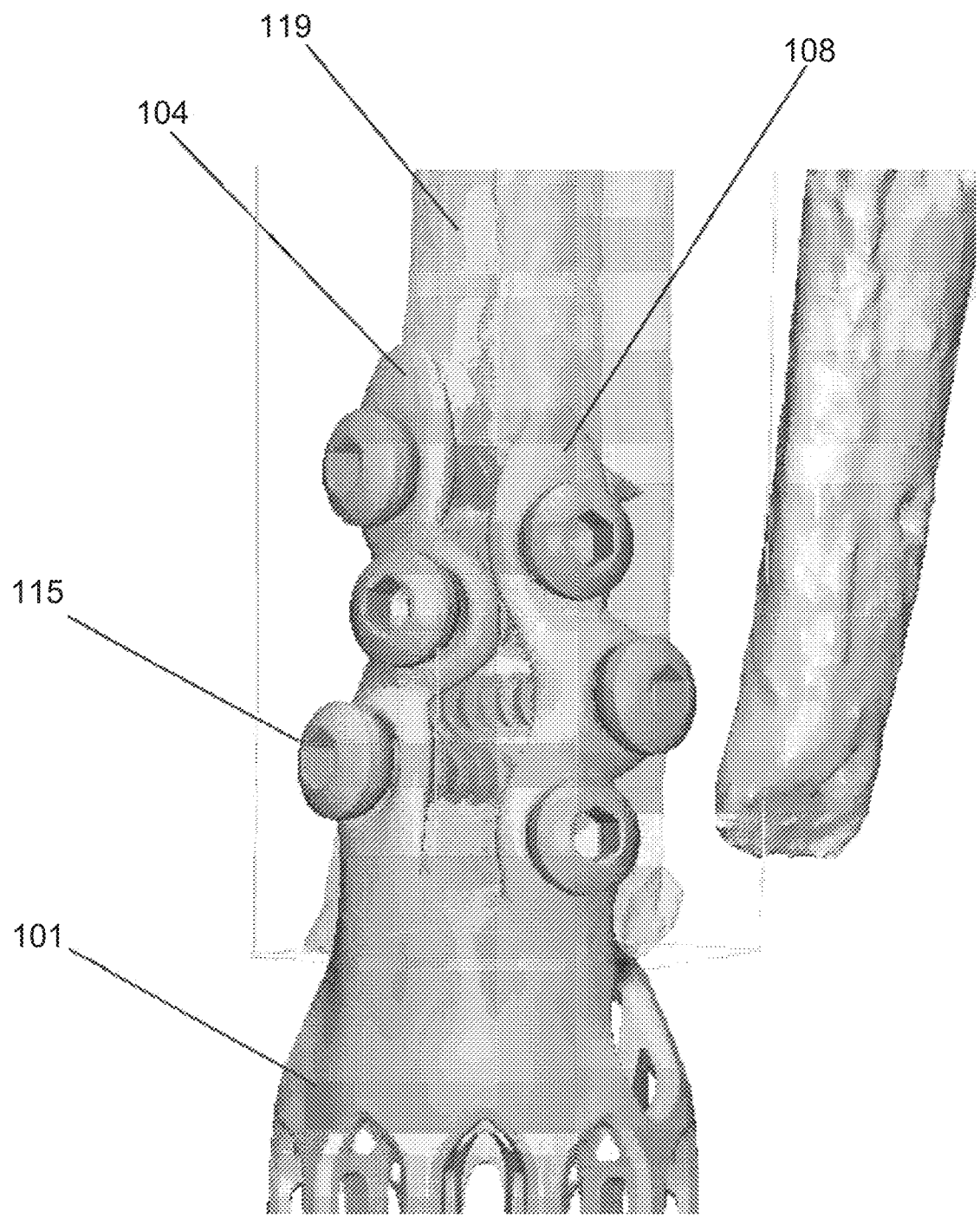
FIG. 26 is a view of the seventh embodiment coupled to a bone.

FIG. 26 shows a view of the device 100 having body section 101 coupled to a person's bone such as a tibia 119. Elongated sections 104 and 108 are shown having fasteners 115 coupled thereto.

Figure 27:
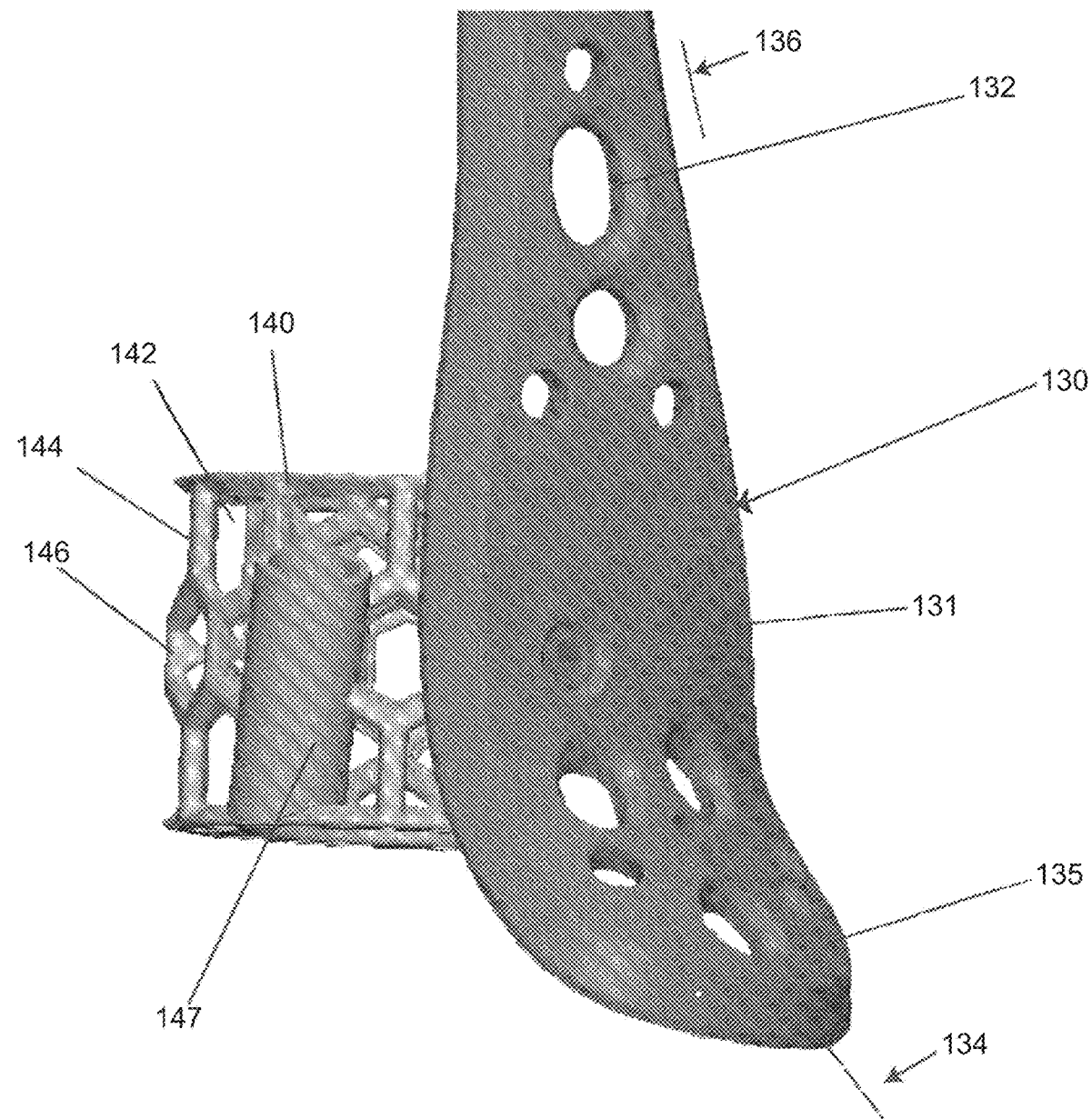
FIG. 27 is a side view of an eighth embodiment.

FIG. 27 is a side view of another embodiment 130 which shows a plate 131 having a plurality of screw holes 132. Plate 131 extends along a substantially elongated axis 136 and bends towards a partially transverse axis 134 via a curved or flared extension 135. The angle of bend can be between 5 degrees to 60 degrees of bend off of a longitudinal axis 136. Coupled to the plate 131 is a cage 140. Cage 140 has a plurality of holes 142, a plurality of struts 144, and a plurality of cells 146. There is also a screw channel 147 coupled to cage 140 as well. This embodiment 130 can be a single printed piece or formed from two pieces wherein cage 140 is coupled together with plate 131 with a connection screw.

Figure 28:
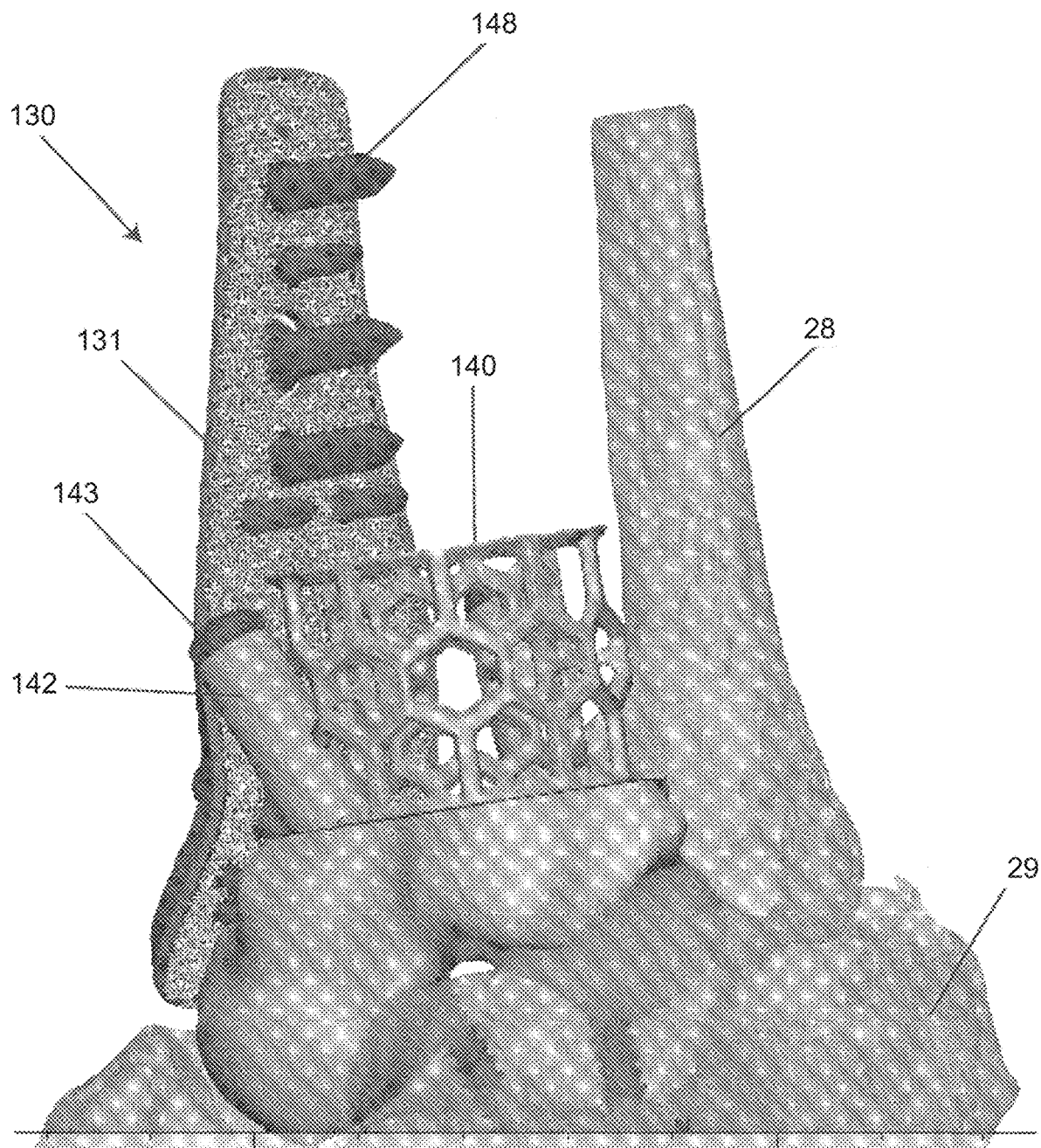
FIG. 28 is a side view of the eighth embodiment coupled to a foot.

FIG. 28 shows a view of the device 130 having plate 131, screw channel 142 receiving a fastener 143, as well as a plurality of additional fasteners 148 for securing the bone fixation device 130 to an adjacent bone such as a tibia 28. There is also shown cage 140 for fixing the device to both the tibia 28 and to a person's foot 29.

Figure 29:
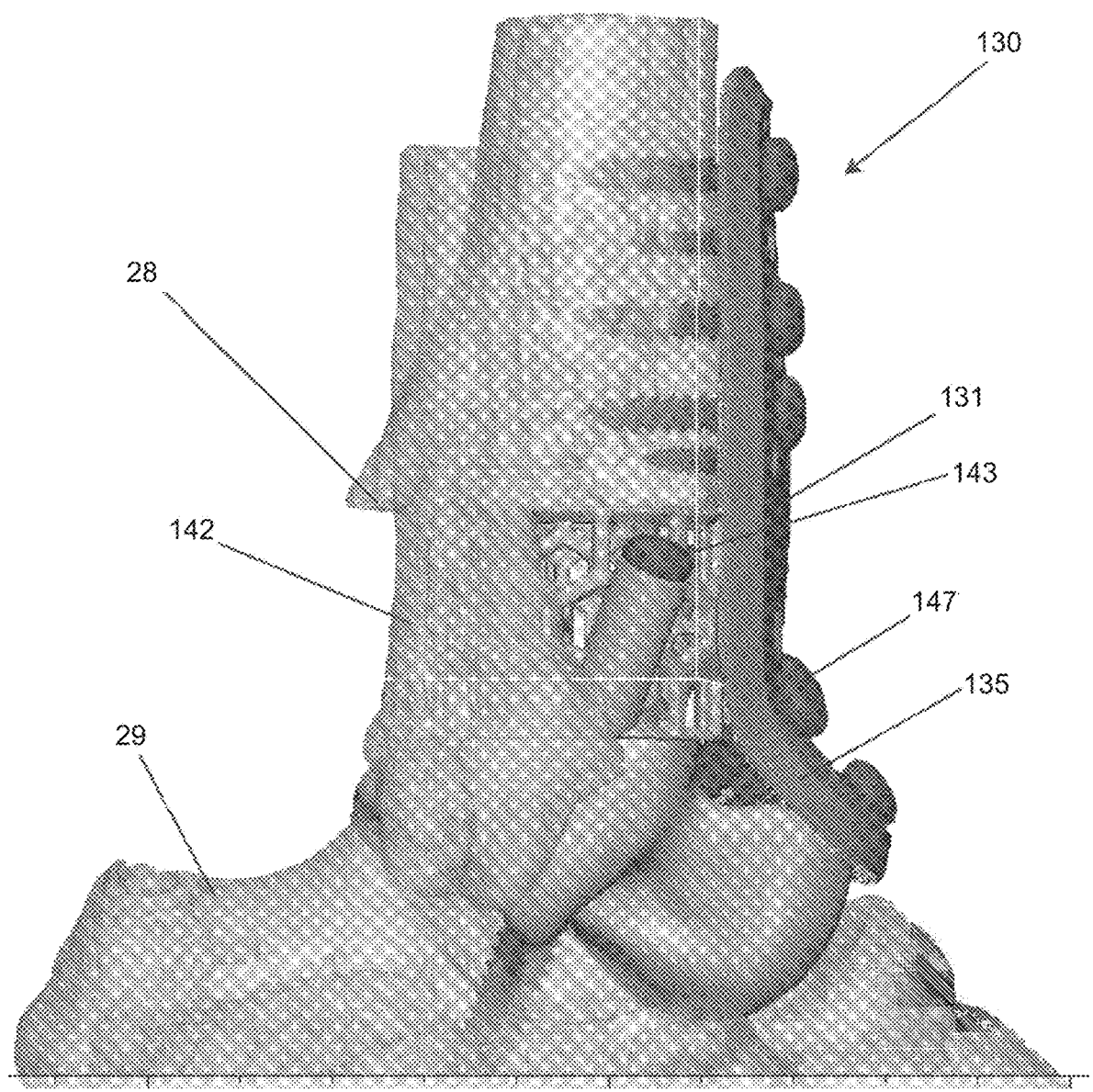
FIG. 29 is another side view of the eighth embodiment coupled to the foot.

FIG. 29 shows a side view of the device 130 secured to a person's body with plate 131 being secured to tibia 28 and also to a person's foot 29. A plurality of fasteners 147 is shown as well as flared extension 135 extending out from tibia 28 and towards the user's foot 29. Screw channel 142 is shown receiving fastener 143 as well.

Figure 30:
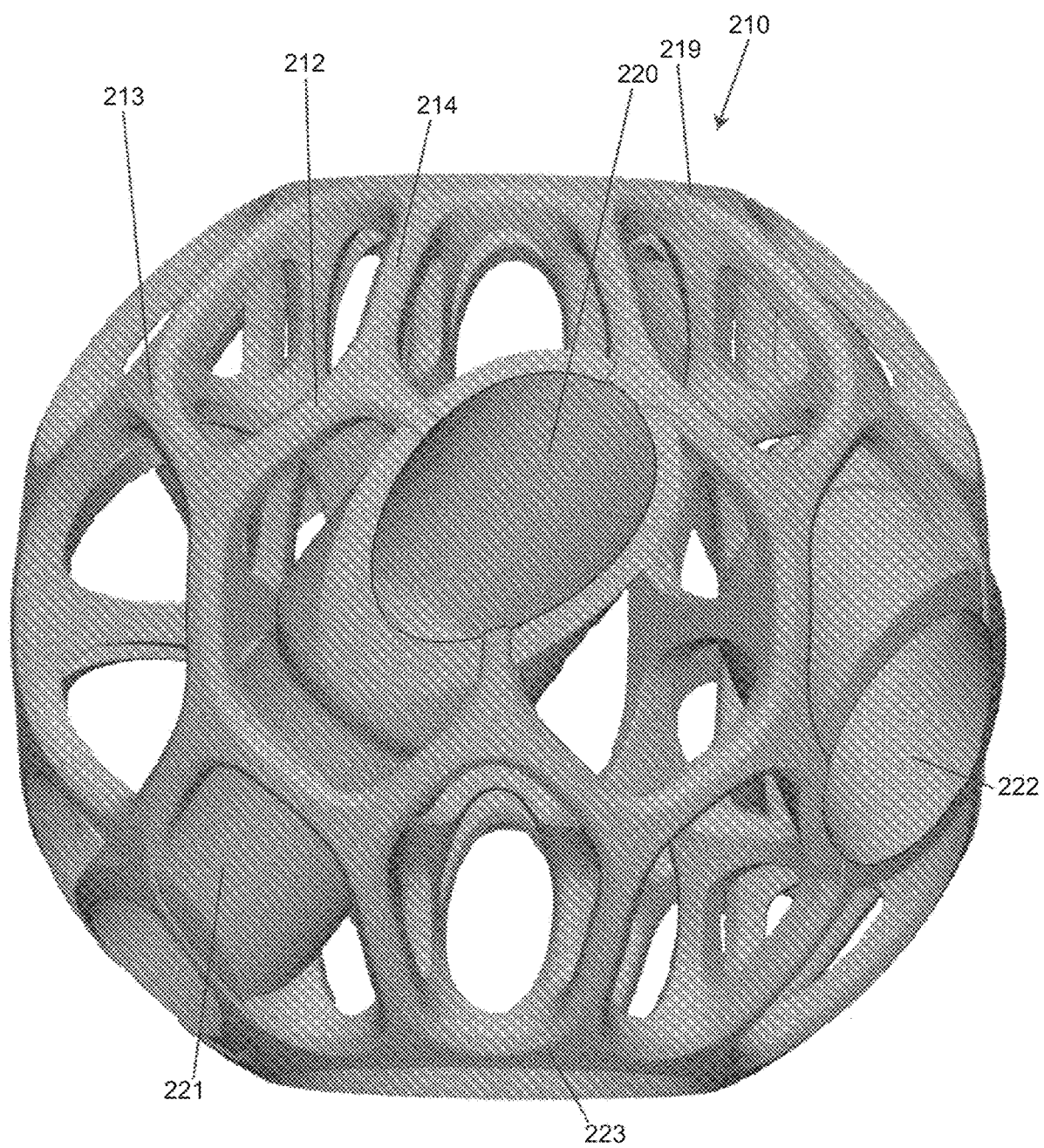
FIG. 30 is a view of another embodiment of an outer shell or cage.

FIG. 30 shows another embodiment which shows a cage 210 having struts 214, including laterally extending struts 212 and 213. In addition there are a plurality of screw channels 221 and 222 having openings 220 which are formed to receive fasteners or screws. These screw channels are disposed inside of the cage 210 rather than being positioned radially outside of the cage 210 as shown in FIG. 1.

Figure 31:
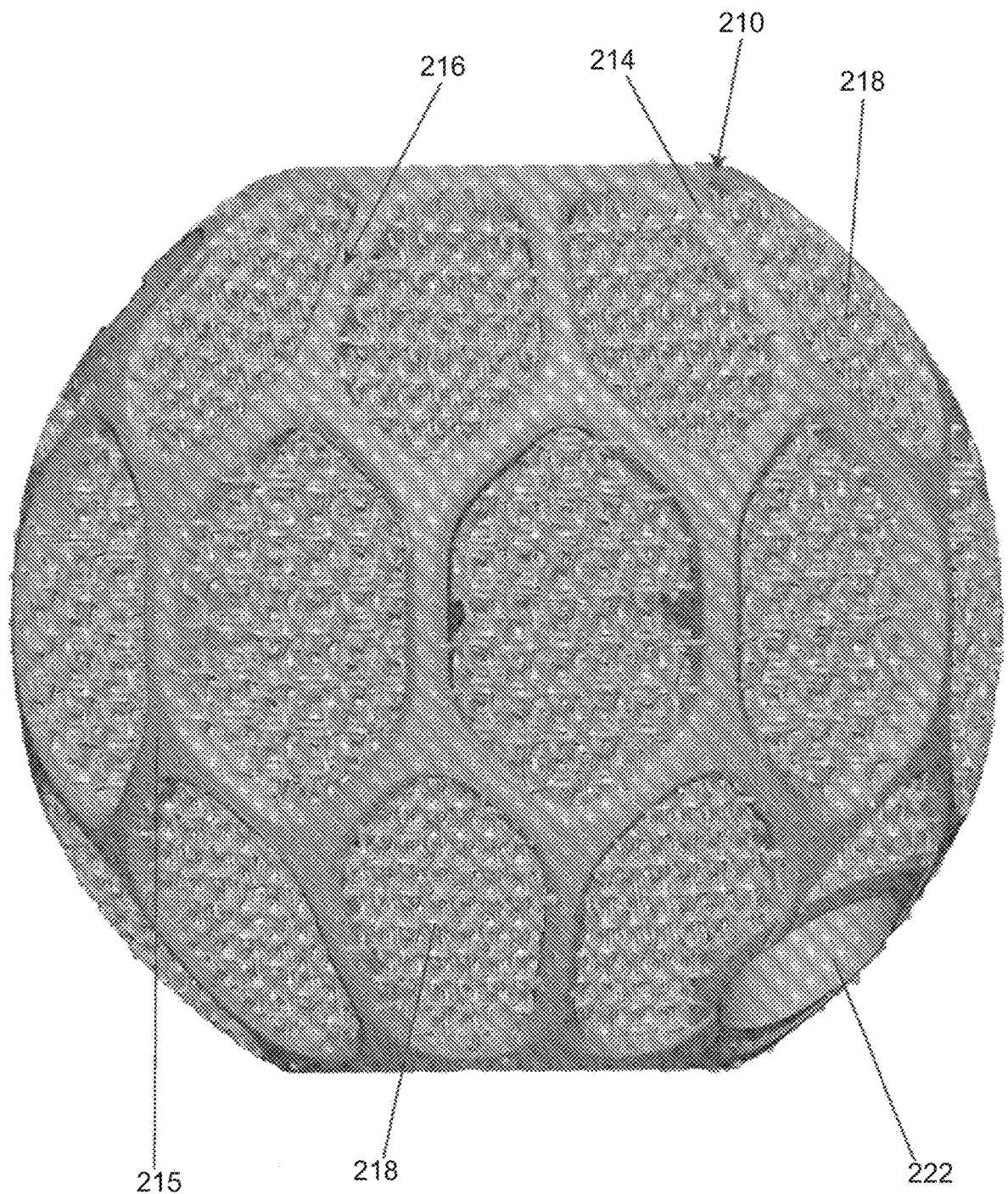
FIG. 31 is a view of the outer shell or cage with a mesh screen disposed inside.

FIG. 31 shows the embodiment of the cage shown in FIG. 30 with mesh 218 disposed inside of cage 210 having struts 214. Mesh 218 is configured to extend radially outside of struts 214 of cage 210 so that they form interaction points with an adjacent bone. Each of these struts join at different join points 215 to form patterned cells such as cells 216.

Figure 32:
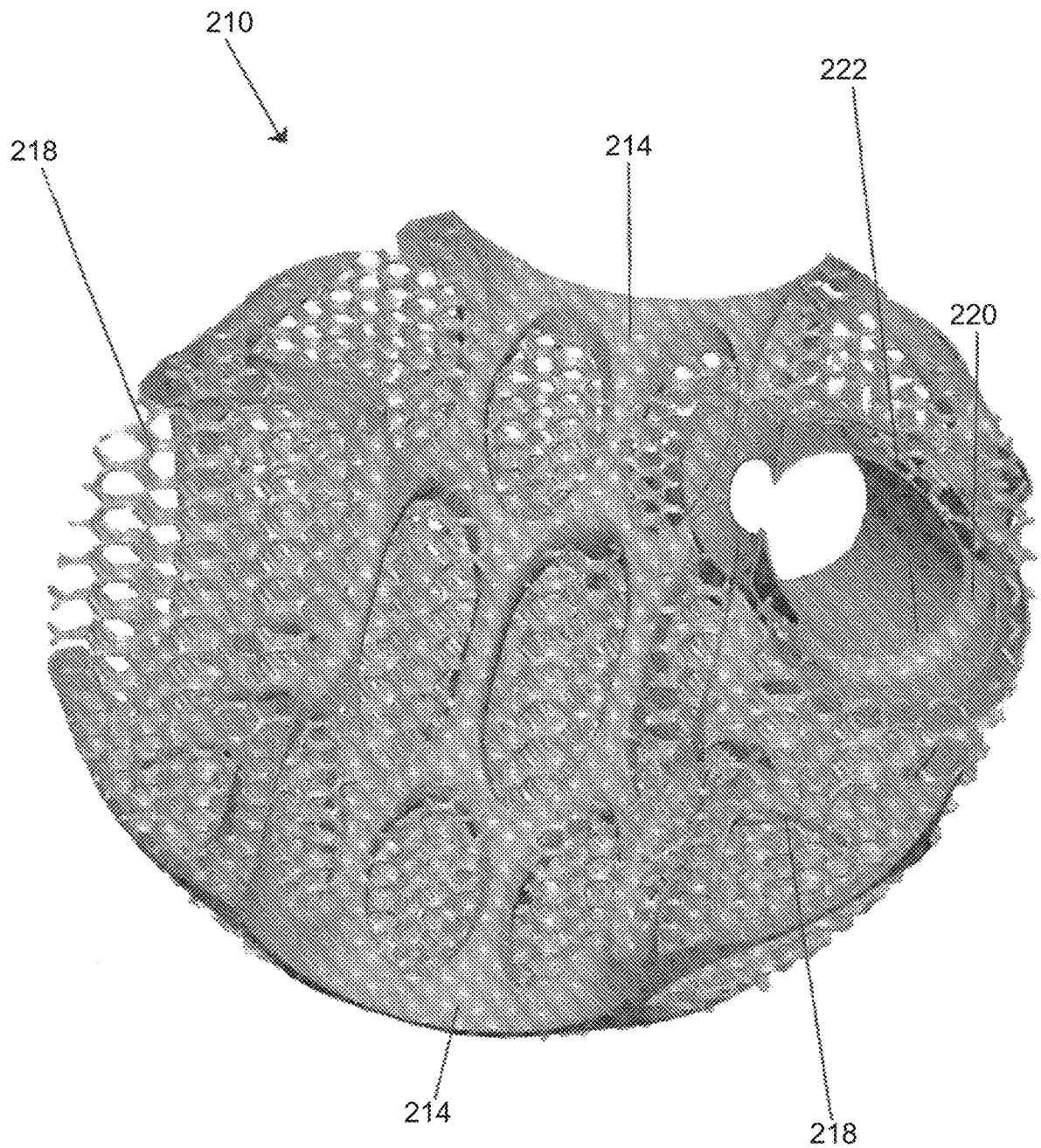
FIG. 32 is a cross-sectional view of the mesh screen taken along a vertical plane

FIG. 32 shows a cross sectional view of the cage 210 which shows mesh 218, as well as struts 214. This view also shows a section of a screw or fastener channel 221 having hole 220 disposed therein. Mesh 218 is shown sectioned off, while struts 214 are also shown.

Figure 33:
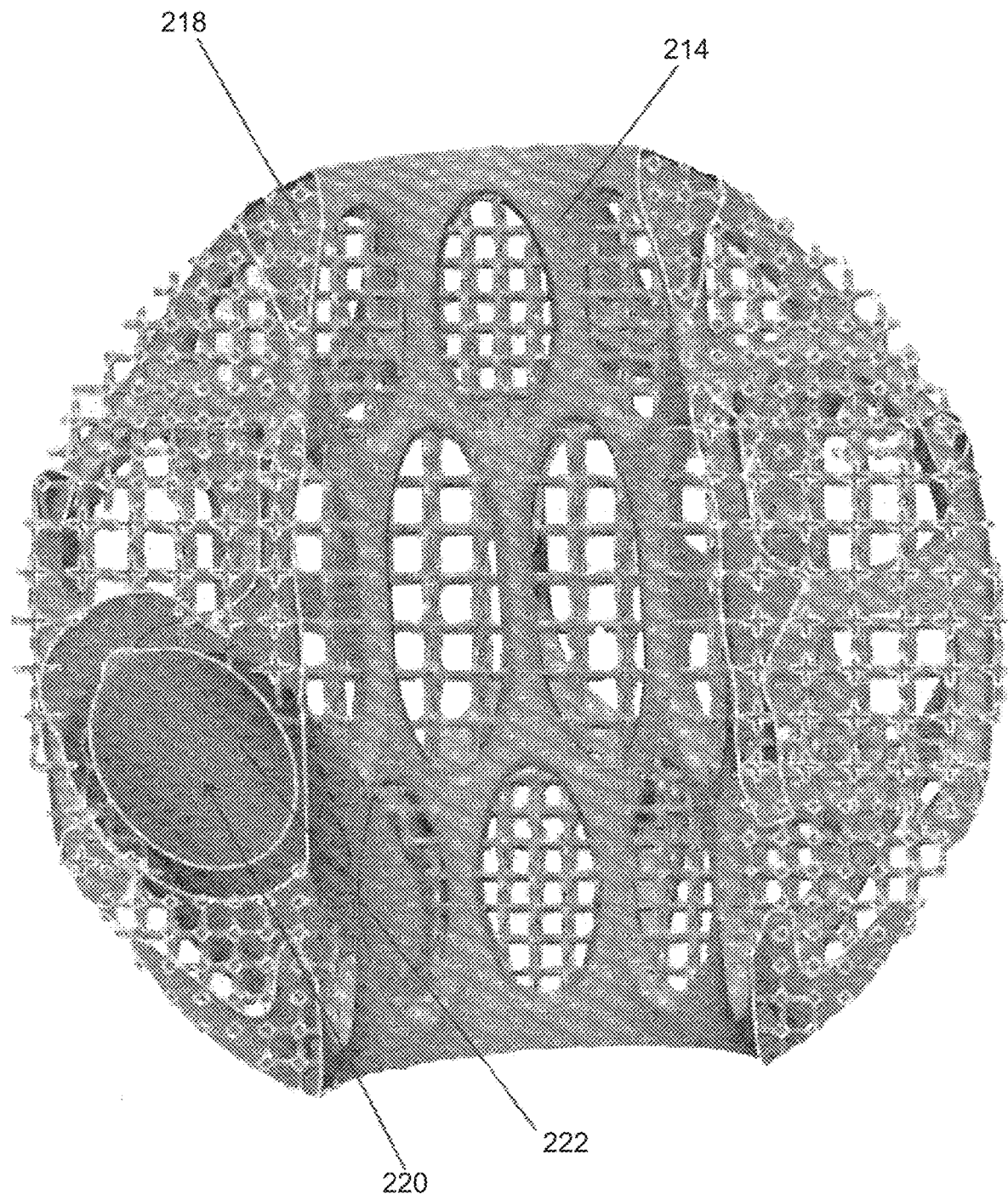
FIG. 33 is another cross-sectional view of the implant of FIG. 31 taken along another vertical plane.

FIG. 33 shows another cross sectional view of the cage 210 which shows mesh 218, as well as struts 214. This view also shows a section of a screw or fastener channel 222 having hole 220 disposed therein. Mesh 218 is shown sectioned off, while struts 214 are also shown.

Figure 34:
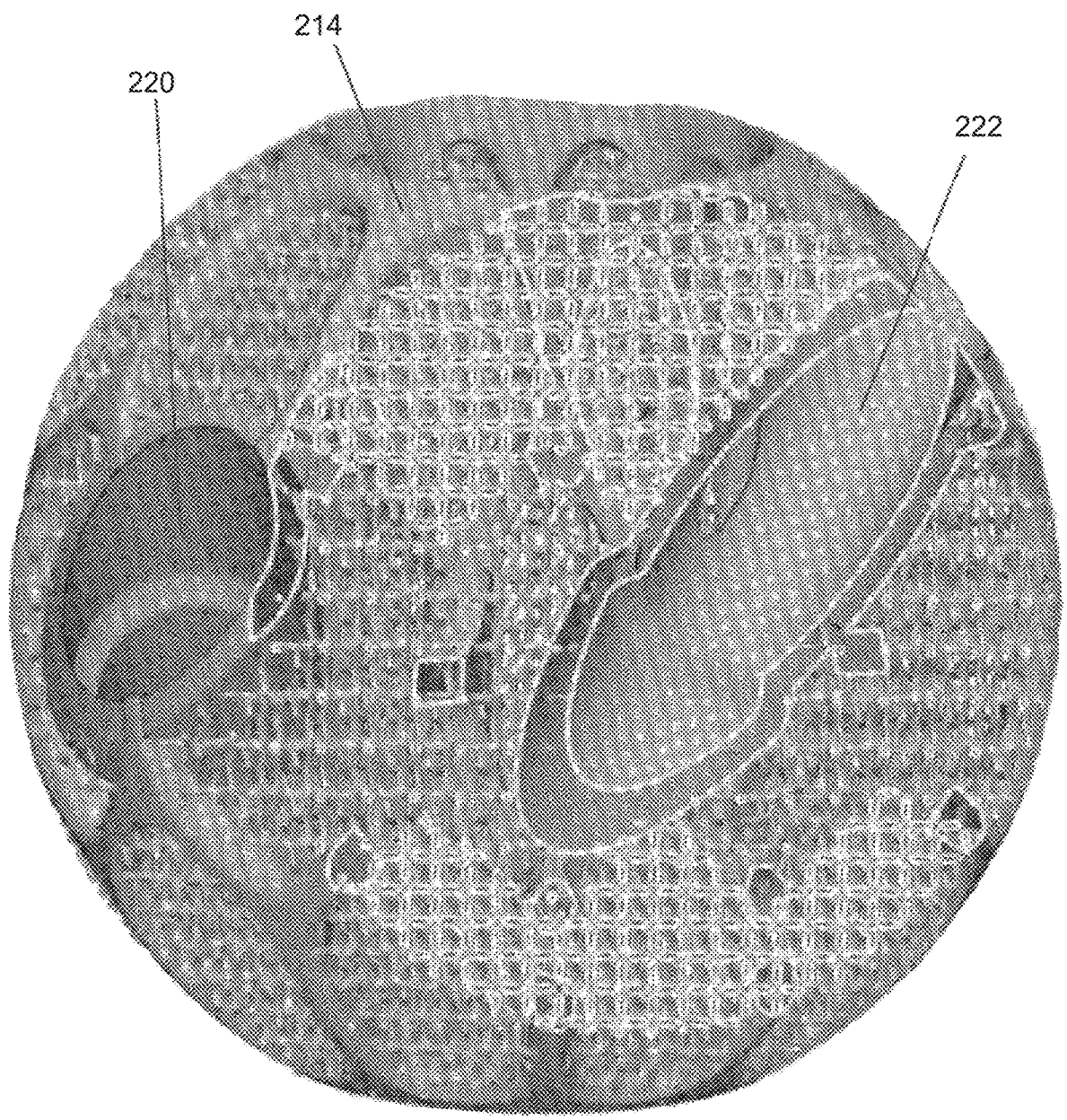
FIG. 34 is a cross-sectional view of another slice of the implant.

FIG. 34 shows a side tangential cross-sectional view which shows screw openings or hole 220 formed in channels 221 and 222. Struts 214 are also shown along with mesh screen 218 as well.

Figure 35:
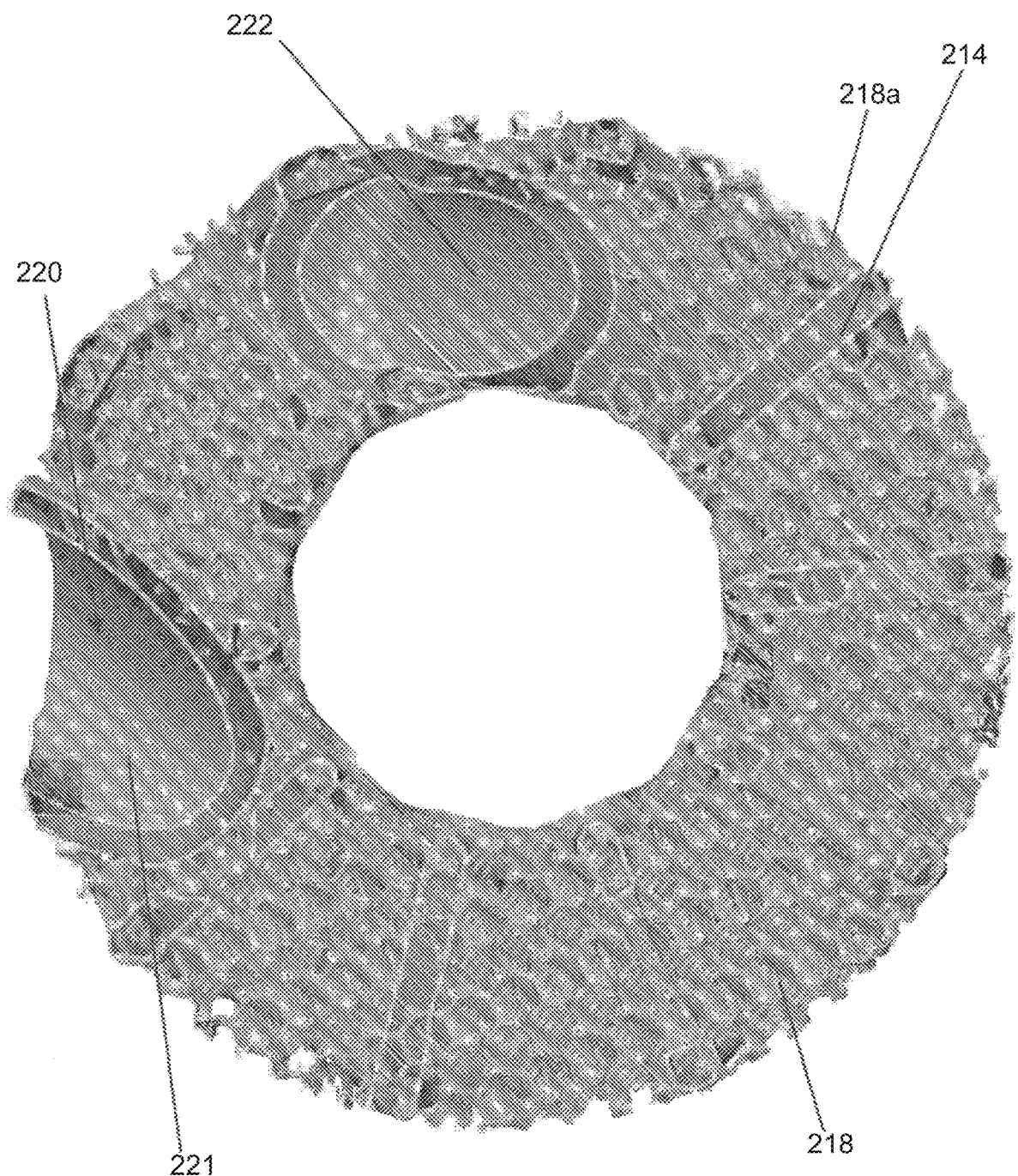
FIG. 35 is a top view of the implant taken along a horizontal plane.

FIG. 35 shows a top cross-sectional view of the embodiment showing screen 218 along with channels 221 and 222 having screw holes 220 disposed therein. The shape of this design is substantially similar to that of the design of FIG. 1 with the exception of the channels 221 and 222 being disposed inside of the cage rather than being disposed external from the cage. In addition, from this view it is shown that at least portions 218a of the mesh screen 218 extend radially outside of or beyond associated struts such as struts 214.

With the above designs there results an ankle fusion cage that can be manufactured with 3D Printing technology. The device can have a variable honey comb lattice structure with selectively smaller pore size on the bone surfaces. While a variable honeycomb structure is proposed alternative embodiments can be of any suitable shape with either a pre-set pore size of a variable pore size. As shown above, the cage and the plates have various locations for screws to go through and to fasten into the bone segments. In these embodiments, the lattice always sits above the surface of the structural frame so it is in contact with the bone. The structure allows for an intramedullary nail to go through the device. Because the device can be printed it can be customized per patient based upon an initial CT scan of the patient.

Using this type of process, a doctor can take an initial image of a region of the body such as a finger joint, an ankle, a knee or a site of a fracture. Based upon the patient's weight, whether they are a smoker, their bone density, diet, age, etc., the doctor or medical professional can create a specialized temporary trial that can be originally printed to fit the patient's needs. This printing can be customized to fit the surface morphology of the bone in the fracture site as well.

With the fastening of the device to a user, instead of a fastener going through it due to a lack of bone, an anterior plate can be secured using a connection screw to the structure.

Another option is to have a polished portion extending from the cage to slide against adjacent sections. The polished portion can be formed from the body section such as body section 81 or plate section 47.

The cage such as any one of cage 12 and/or 42, or 61 is of a design that incorporates a spherical interface with bone segments it comes in contact with. Thus, the top and/or the bottom of the cage will have a general spherical shape that transitions to a somewhat cylindrical body. This is due to using existing acetabular reamers that are available in most hospitals as part of total hip systems.

Accordingly, while at least one embodiment of the present invention have been shown and described, it is to be understood that many changes and modifications may be made thereunto without departing from the spirit and scope of the invention as defined in the appended claims.

What is claimed is:

1. A bone fixation device comprising:
   a body section having a longitudinal axis and comprising an end cap portion that defines a first longitudinal end of the device and a substantially cylindrical body portion extending longitudinally from the end cap portion that comprises an internal cavity that is open at a longitudinal end of the body portion, wherein the end cap portion caps off the internal cavity at the first longitudinal end of the device with the longitudinal axis intersecting the end cap portion, and the longitudinal end of the body portion defines a longitudinal end of the body section;
   at least one fastening portion extending longitudinally from a portion of the longitudinal end of the body portion in a direction extending away from the end cap portion and defining a second longitudinal end of the device, said at least one fastening portion being longitudinally-elongated and comprising a plurality of longitudinally-spaced screw holes; and
   a mesh disposed within the internal cavity on internal surfaces of the body portion,
   wherein the body section is configured to fit over a portion of a bone such that the end cap portion forms an end structure for the bone.

2. The bone fixation device as in claim 1, wherein the body portion comprises a plurality of longitudinally-spaced fastening holes.

3. The bone fixation device as in claim 1, wherein the end cap portion of the body section comprises a substantially spherical outer end surface.

4. The bone fixation device as in claim 1, wherein the body section is configured to fit over an end portion of a tibia bone.

5. The bone fixation device as in claim 1, wherein the body section is configured to fit over an end portion of a leg bone.

6. The bone fixation device as in claim 1, wherein the body section is configured to fit over an end portion of a toe bone.

7. The bone fixation device as in claim 2, wherein the plurality of longitudinally-spaced fastening holes of the body portion comprises a plurality of substantially longitudinally-aligned first fastening holes.

8. The bone fixation device as in claim 7, wherein the plurality of longitudinally-spaced fastening holes of the body portion further comprises a plurality of substantially longitudinally-aligned second fastening holes, the first fastening holes and the second fastening holes being disposed in circumferentially-spaced portions of the body portion.

9. The bone fixation device as in claim 1, wherein the at least one fastening portion comprises a first fastening portion, the first fastening portion comprising a plurality of substantially longitudinally-aligned, longitudinally-spaced screw holes of the plurality of longitudinally-spaced screw holes.

10. The bone fixation device as in claim 9, wherein the body portion comprises a plurality of substantially longitudinally-aligned, longitudinally-spaced first fastening holes that are substantially longitudinally-aligned with the plurality of substantially longitudinally-aligned, longitudinally-spaced screw holes of the first fastening portion.

11. The bone fixation device as in claim 10, wherein the body portion comprises a plurality of substantially longitudinally-aligned, longitudinally-spaced second fastening holes, the first fastening holes and the second fastening holes being disposed in circumferentially-spaced portions of the body portion.

12. The bone fixation device as in claim 10, wherein the first fastening portion comprises an inner bone engagement surface configured to engage an outer surface of the bone when the body section is fit over the portion of the bone.

13. The bone fixation device as in claim 12, wherein the mesh is further disposed on the inner bone engagement surface.

14. The bone fixation device as in claim 1, wherein the at least one fastening portion comprises a first fastening portion that comprises an inner bone engagement surface configured to engage an outer surface of the bone when the body section is fit over the portion of the bone.

15. The bone fixation device as in claim 14, wherein the first fastening portion is configured as a bone plate portion.

16. The bone fixation device as in claim 14, wherein the inner bone engagement surface is substantially aligned with a portion of the inner surfaces of the body portion.

17. The bone fixation device as in claim 14, wherein the mesh is further disposed on the inner bone engagement surface.

18. The bone fixation device as in claim 14, wherein the at least one fastening portion comprises a second fastening portion that is configured to extend into an interior of the bone when the body section is fit over the portion of the bone.

19. The bone fixation device as in claim 1, wherein the at least one fastening portion comprises a first fastening portion that is configured to extend into an interior of the bone when the body section is fit over the portion of the bone.

20. The bone fixation device as in claim 19, wherein the first fastening portion comprises a plurality of the plurality of longitudinally-spaced screw holes.

21. The bone fixation device as in claim 19, wherein the mesh is further disposed on at least a portion of the first fastening portion.

* * * * *